US008546093B2

United States Patent
Song et al.

(10) Patent No.: US 8,546,093 B2
(45) Date of Patent: Oct. 1, 2013

(54) DETECTION METHOD FOR METHICILLIN RESISTANT STAPHYLOCOCCUS AUREUS

(75) Inventors: Hyung-Geun Song, Cheongju-si (KR); Sang-Soon Yoon, Iksan-si (KR); Hae-Jung Kim, Iksan-si (KR); Gil-Yong Jee, Gyeryong-si (KR); Mi-Hyang Shin, Seongnam-si (KR); Yu-Ri Moon, Cheongju-si (KR)

(73) Assignee: Dinona Inc., Seoul (KR)

( * ) Notice: Subject to any disclaimer, the term of this patent is extended or adjusted under 35 U.S.C. 154(b) by 0 days.

(21) Appl. No.: 13/255,115

(22) PCT Filed: Jun. 24, 2009

(86) PCT No.: PCT/KR2009/003412
§ 371 (c)(1),
(2), (4) Date: Sep. 7, 2011

(87) PCT Pub. No.: WO2010/104245
PCT Pub. Date: Sep. 16, 2010

(65) Prior Publication Data
US 2012/0070851 A1 Mar. 22, 2012

(30) Foreign Application Priority Data
Mar. 11, 2009 (KR) .................... 10-2009-0020935

(51) Int. Cl.
*G01N 33/577* (2006.01)
*C12N 5/16* (2006.01)
*C07K 16/12* (2006.01)

(52) U.S. Cl.
USPC .................. 435/7.33; 424/130.1; 424/139.1; 424/150.1; 530/387.9; 530/388.1; 530/388.4; 435/7.1; 435/7.2; 435/7.32

(58) Field of Classification Search
None
See application file for complete search history.

(56) References Cited

FOREIGN PATENT DOCUMENTS

EP 875578 A2 * 11/1998
WO 88-02028 3/1988

OTHER PUBLICATIONS

Kohler and Milstein, "Continuous cultures of fused cells secreting antibody of predefined specificity" Nature Volume, 256: 495-497 (Aug. 7, 1975).
Harlow and Lane, "Antibodies: A Laboratory Manual" Cold Spring Harbor Laboratory, New York (1988).
Larsson A, et al., "Novel Latex Agglutination Method with Chicken Anti-Protein A for Detection of *Staphylococcus aureus* Infections." Journal of Clinical Microbiology vol. 27, No. 12, p. 2856-2857 (Dec. 1989).
Roger Lindmark, et al. "Binding of Immunoglobulins to Protein A and Immunoglobulin Levels in Mammalian Sera" Journal of Immunological Methods, 62:1-13. (1983).
R. A. Goldsby, T. J. Kindt, B. A. Osborne, Kuby Immunology, 4th ed. (W. H. Freeman and Company), p. 162 (2000).
Larsson A, et al., "Chickent Anti-Protein A for the Detection and Capturing of Protein A from *Staphylococcus aureus* in the Presence of Absence of Mammalian IgG" Hybridoma, vol. 11, No. 2, p. 239-43 (1992).
Shimomura R, Tsutsumi Y. "Histochemical identification of Methicillin-resistant *Staphylococcus aureus*: contribution to preventing nosocomial infection." Seminars in Diagnostic Pathology. vol. 24, No. 4, p. 217-226 (Nov. 2007).
Ryffel C, et al., "Sequence comparison of mecA genes isolated from methicillin-resistant *Staphylococcus aureus* and *Staphylococcus epidermidis*" Gene, 94(1):137-138 (1990).
International Search Report of PCT/KR 2009/003412 dated Dec. 14, 2009.

* cited by examiner

*Primary Examiner* — Robert A Zeman
(74) *Attorney, Agent, or Firm* — Lexyoume IP Meister, PLLC.

(57) ABSTRACT

The present invention relates to an antibody against a protein specifically expressed in methicillin-resistant strains of *Staphylococcus aureus* (MRSA), and a method and a kit for detecting MRSA. The present invention enables a fast and accurate detection of MRSA by using both a PBP2a-specific antibody for the detection of PBP2a and a Protein A-specific antibody for the detection of Protein A.

4 Claims, 15 Drawing Sheets

Fig.2

Penicillin-binding protein 3 [pbp3] [Bacillus thuringiensis subsp. konkukian]   661 AA align Score = 394 bits (1012), Expect = e-108
Identities = 225/626 (35%), Positives = 363/626 (57%), Gaps = 29/626 (4%)

```
Query  40   KNFKQVVKDSSYISKSDNGEVEMTERPIKIYNSLGVKDINIQDRXXXXXXXXXXRVDAQY  99
            +F++Y  S +K D  +E TE+ K+Y+ + VK++ ++                  + +
Sbjct  39   QKFAEMYDQLSEKAKKDISKKEFTEKYEKIYSGIEVKNLKVEAGEVKEDKKDEGPIPFKV  98

Query  100  KIKTNYGNIDRNVQFNFVKEDG---MWKLDWDHSVIPGMQKDQSIHIENLKSERGKIL  155
            +T G++  +   +KE DG    WK+DW   IPGM KD  +++  + +RG+I
Sbjct  99   SMDTVGGKINFGHEAKMVKEKDGDKESWKVDWTPDFIFPGMTKDSKVRMQTTEPKRGEIY  158

Query  156  DRNNVELANTGTHMRLGIVPKNV---SKKDYKAIAKELSISEDYINNK----WKIGYKM  208
            DRN  LA G  +G++P+ +  + +  + AK L++S+ I+ K      W+K GY+
Sbjct  159  DRNGKGLATNGKASEIGLIPEKLGDTAPQTKETVAKLLNMSVEEIDQKLAAKWVKPGYL  217

Query  209  IPSFHFKTVKKMDEYLSDFAKKFHLTTNETESRNYPLEKATSHLLGYVGPINSEELKQKE  268
            +P      +Y+       ++T    R YPL + A +HL GY+G +N+E+LK    +
Sbjct  218  VPIGILPEGATQNTYIDLPG----VSTKPVNVRTYPLGEAAAHLTGYIGKVNAEDLKTLQ  273

Query  269  YKGYKDDAVGKKGLEKLYDKKLQHEDGYRVTIVDDNSNTIAHTLIEKKKKDGKDIQLTI  328
            KGY+ D  +GK GLE++ ++KL+ +  G RV+ D    I+ L+    DG+++ LTI
Sbjct  274  KKGYQADDPVGKAGLEQVLEEKLRGKKGGRVFVEDAQGKEIKN-LAKTDAVDGENVTLTI  332

Query  329  DAKVQKSLYNNMKNDYGSGTAIHPQTGELLALVSTPSYDVYPFMYGMSNEEYNKLTEDKK  388
            D+ VQ+  YN MK+ GS  A++P++GE LALVS+P+YD     G+S +        D K
Sbjct  333  DSAVQEKTYNEMKGEAGSSAAINPKSGETLALVSSPAYDPNIIARGTSKAQREAWNNDPK  392

Query  389  EPLLNKFQITTSPGSTQKILTAMIGLNNKTLDDKTSYKIDGKGWQKDKSWGGYNVTRYEV  448
            +P+ N+F   +PGS  K +TA IGL   KT+D K  KI+G  WKD SWG Y VTR +
Sbjct  393  KPMTNRFTQLSVPGSVFKPITAAIGLETKTIDPKEELKIEGLKWTKDSSWGNYYVTRVKD  452

Query  449  VNGNIDLKQAIESSDNIFFARVALELGSKKFEKGMKKLGVGEDIPSDYFFYNAQISNKNL  508
              N ID +A++ SDNI+FA+ AL++G  KF    KK G  E +P +Y+F  ++ +N +
Sbjct  453  AN-RIDFDKAMKYSDNIYFAQEALKIGKDKFMSEAKKFGFDEKLRIEYGFPASKIANDGI  511

Query  509  DNEILLADSGYGQGEILINPVQILSIYSALENNGNINAPHLLK-DTKNIKVWKKNIISKEN  567
            N+I +AD+G+GQG++L+ P+ +  Y+ + N+GNI +P+++K D + K VWK+ N+ ISK N
Sbjct  512  KNDIQMADTGYGQGQVLMTPLHLALTYAPIVNDGNIPSPYIIKTDKQPKVWKENVSKGN  571

Query  568  INLLNDGMQQVVN-----KTHKEDIYRSYANLGKSGTAELKMKQGESGRQIGWFISYD  621
            ++L M +V+N   K  K D    L GK+GTAELK+ +    G+++GWF ++D
Sbjct  572  QDILKTAMTKVINDPDGTGKIAKID----GMTLAGKTGTAELKVSKEAEGKELGWFAAFD  627

Query  622  KDNPNMMMAINVKDVQDKGMASYNAK  647
              +P+ M++ + ++D V+  G ++  A+
Sbjct  628  LNSPDMVITMMIEDVKGRGGSNIPAE  653
```

Fig.14b
MRSA 1522
MRSA 1641
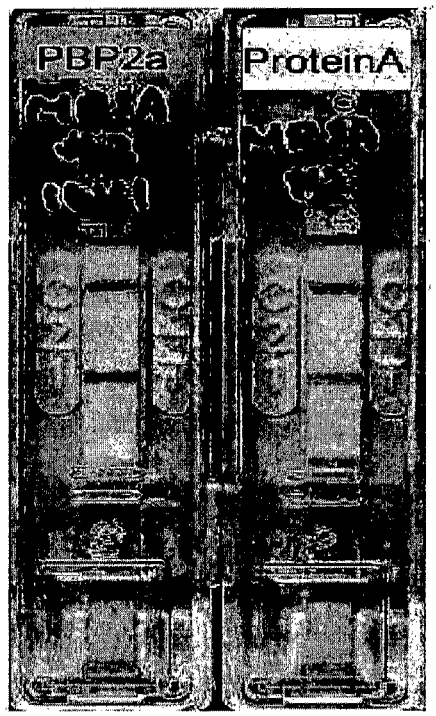
Fig.14c
MRCNS 5252
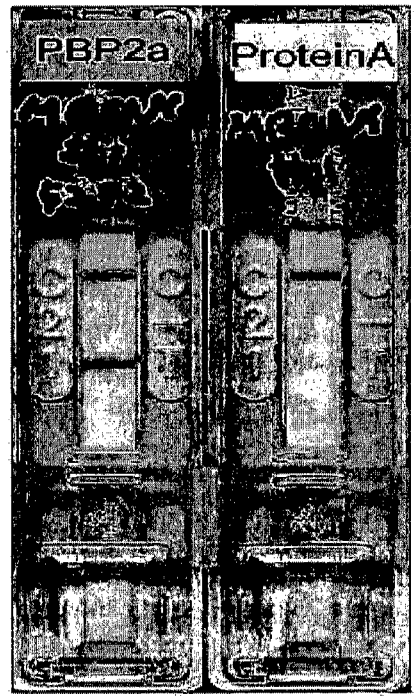
MRCNS 5316
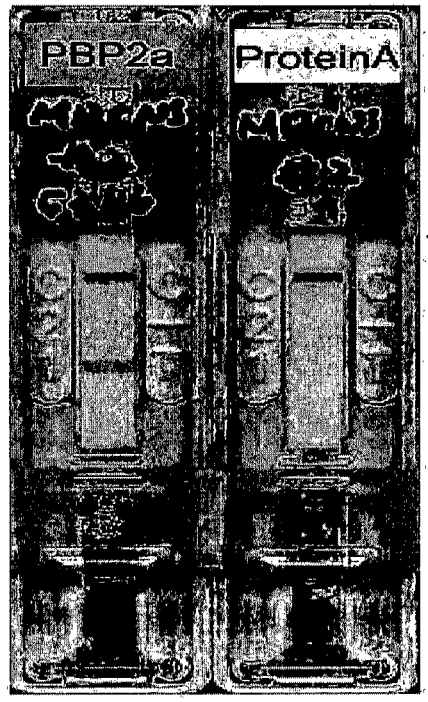

MSSA 560

MSCNS 219      MSCNS 5241

DETECTION METHOD FOR METHICILLIN RESISTANT STAPHYLOCOCCUS AUREUS

TECHNICAL FIELD

The present invention provides an antibody against a protein specifically expressed in methicillin-resistant strains of Staphylococcus aureus (MRSA), and a method and a kit for detecting MRSA comprising the antibody, thereby distinguishing and detecting selectively MRSA from other strains of Staphylococcus aureus a promptly and accurately.

BACKGROUND ART

Staphylococcus aureus (S. aureus) is one of the most common causative organisms of hospital and non-hospital infections. Representative types of Staphylococcus aureus, S. aureus include: Methicillin resistant Staphylococcus aureus (MRSA), Methicillin resistant coagulase negative Staphylococcus (MR-CNS), Methicillin sensitive Staphylococcus aureus (MSSA), and Methicillin sensitive coagulase negative Staphylococcus (MS-CNS). Among these bacteria, the MRSA is one of the most frequent hospital bacteria and is infected with patients having a weak immunity. However, there were only a few antibacterial drugs developed, and thus, the infection rate of the patients by the bacterium is very high.

Currently, MRSA infection can be diagnosed by (1) antibiotics sensitivity tests on the cultured bacteria, (2) detection of genes specific to MRSA from the colonies of cultured bacteria, and (3) detection of proteins specific to MRSA from the colonies of cultured bacteria. While most hospitals use method (1), it takes at least 2-3 days before test results are obtained. For small-sized hospitals, particularly, the method of detecting infection by observing proteins specific to MRSA in the cultured bacteria is hard to be performed as this method may take one or two extra days. As such, antibiotics are often applied without conducting diagnostic tests. In practice, the methods of (2) and (3) are too complicated for general clinics to conduct, such that those are performed for the purpose of research only.

With those currently available methods, detection of MRSA infection is delayed, and it is often the cases that a right time point for treatment is missed or that improper antibiotics are applied. As such, there exists a strong need for development of a method and a kit for detecting MRSA in a prompt and accurate manner.

BRIEF DESCRIPTION OF THE DRAWINGS

FIG. 2 shows amino acid homology among various PBP2a proteins in bacteria which have PBP2a, in order to select a sequence specific to Staphylococcus aureus, according to an embodiment of the present invention.

FIG. 5a is the graph where His-PBP2a was diluted and assayed by ELISA, while FIG. 5b is the graph where the monoclonal antibodies according to the present invention were diluted and assayed by ELISA.

FIG. 7a is the result from immunoblot assay, while FIG. 7b is the result from ELISA.

FIG. 9a shows the result by sandwich ELISA where the monoclonal antibodies of the present invention, as bound to biotin, were used as detection antibodies. FIG. 9b shows the result by sandwich ELISA where the 6G10 monoclonal antibodies of the present invention were used as detection antibodies, along with the '9C6' monoclonal antibodies of the present invention as coating antibodies. FIG. 9c shows the result by sandwich ELISA where His-PBP2a was serially diluted.

FIG. 10a is the test result where lysates collected from 5 strains of MRSA and 1 strain of MSSA were assayed by sandwich ELISA, using an antibody pair constructed from the monoclonal antibodies of the present invention. FIG. 10b shows the result in which PBP2a presence in various strains was examined by sandwich ELISA, using an antibody pair constructed from the monoclonal antibodies of the present invention.

FIGS. 14a to 14e show the detection result of MRSA using the monoclonal antibodies of the present invention and anti-Protein A polyclonal antibodies. FIG. 14a is the result by sandwich ELISA, while FIGS. 14b to 14e are the result by lateral flow immunoassay.

DETAILED DESCRIPTION

Technical Problem

Figure 1A:
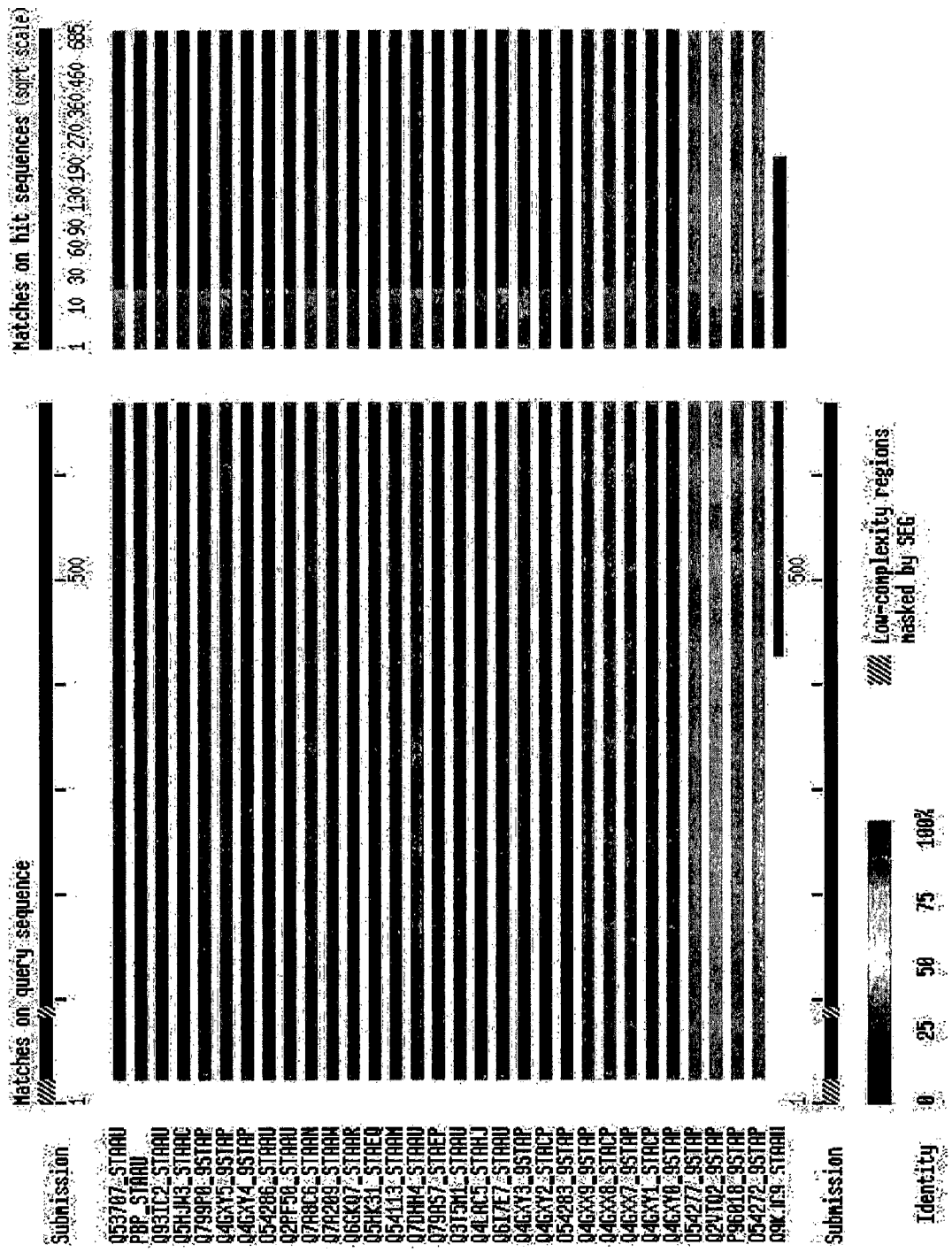
FIGS. 1a to 1c show the interspecies homology of amino acid sequence for penicillin-binding protein 2a (hereinafter PBP2a) among the strains of Staphylococcus aureus, according to an embodiment of the present invention.

Recognizing the problems stated above, the present inventors have studied the detection methods for MRSA infection and provide the present invention, which enables the detection of MRSA in a fast and accurate manner by using both PBP2a-specific monoclonal antibodies and Protein A-specific antibodies.

Therefore, an object of the present invention is to provide a monoclonal antibody specifically binding to a polypeptide comprising a penicillin-binding protein 2a(PBP2a) fragment, wherein the PBP2a fragment has the amino acids of SEQ ID NO: 1.

Another object of the present invention is to provide a hybridoma cell producing the monoclonal antibody, in which said hybridoma cell has accession number of KCLRF-BP-00202, KCLRF-BP-00203, or KCLRF-BP-00204.

Further object of the present invention is to provide a method for MRSA detection comprising the steps of: contacting a test sample with a PBP2a-specific antibody and a Protein A-specific antibody; and detecting the formation of an antigen-antibody complex.

Still object of the present invention is to provide a kit for MRSA detection which comprises a PBP2a-specific antibody and a Protein A-specific antibody.

Still object of the present invention is to provide a composition for MRSA detection which comprises a PBP2a-specific antibody and a Protein A-specific antibody.

Technical Solution

To accomplish the objects stated above, the present invention provides a monoclonal antibody specifically binding to a polypeptide comprising a PBP2a fragment. Preferably, the PBP2a fragment has the amino acid sequence of SEQ ID NO: 1.

The present invention also provides a hybridoma cell which produces the monoclonal antibody. The hybridoma cell has accession number of KCLRF-BP-00202, KCLRF-BP-00203, or KCLRF-BP-00204.

The present invention also provides a method for MRSA detection comprising the steps of: contacting a test sample with a PBP2a-specific antibody and a Protein A-specific antibody; and detecting the formation of an antigen-antibody complex.

The present invention also provides a kit for methicillin resistant *Staphylococcus aureus* (MRSA) detection which comprises a PBP2a-specific antibody and a Protein A-specific antibody.

The present invention also provides a composition for methicillin resistant *Staphylococcus aureus*(MRSA) detection which comprises a PBP2a-specific antibody and a Protein A-specific antibody.

Below is a more detailed description of the present invention.

For the present invention, the term "monoclonal antibodies" refer to one as widely known in the field to which present invention is belong. A monoclonal antibody displays high specificity, i.e., specific to a single antigenic site (monospecific). Unlike a polyclonal antibody including different antibodies—each of the antibodies recognizing each different epitope—a monoclonal antibody recognizes a single epitope per antigen. Monoclonal antibodies according to the present invention can be prepared by conventional cloning and cell-fusion techniques. For instance, natural or human monoclonal antibodies can be produced by injecting immunogens (antigens) of interest into wildtype- or bred mice (i.e., BALB/c).

Such antibodies can be injected alone or in combination with an adjuvant, can be expressed through a vector, or can induce immune response in the form of DNA or fusion protein. A fusion protein can be a peptide-coupled carrier protein as induced by immune responses. The examples of such carrier protein include, but not limited to, β-galactosidase, glutathione S-transferase, keyhole limpet haemocyanin (KLH), bovine serum albumin. In that case, peptide functions as a hapten to carrier protein.

A preparation method for monoclonal antibody is briefly provide in the below. After boosting the selected animal, the spleen is removed to collect the spleen cells. Then, the spleen cells are fused with myeloma cells, using the techniques known in the field to which the present invention belongs [Kohler and Milstein, Nature 256: 495-497 (1975); and Harlow and Lane, Antibodies: A Laboratory Manual, Cold Spring Harbor Laboratory, New York (1988)]. With the hybridoma obtained, cloning is performed by conventional techniques, for example, by using limiting dilution, and then the clones producing desired monoclonal antibodies are cultured. Monoclonal antibodies provide the benefit of improving the selectivity and specificity to diagnostic and analytic techniques that utilize antigen-antibody complexes. Another benefit is that such monoclonal antibodies are contamination-free as they are produced through hybridoma cultivation.

For the present invention, the term "hybridoma" is widely known to those skilled in the art and refers to the cell produced as a result of fusion between antibody-producing cell and immortal cells. For instance, a hybridoma can be cells resulting from the fusion with myeloma cells. Hybridomas are capable of continuing to supply antibodies.

For the present invention, the term "detection label" refers to a label used for the detection of immune-complexes. Examples of such detection labels include but are not limited to: radioactive isotopes, enzymes, chemiluminescent compounds, fluorescent substances like fluorescein, phycobiliproteins, lanthanide chelates, rhodamines, enzyme cofactors, and biotins.

For the present invention, the term "test sample" refers to any biological materials including cells, tissues, and biofluid.

For the present invention, the term "antigen-antibody complex" refers to a complex of PBP2a (or Protein A) and a corresponding antigen which recognizes the PBP2a (or Protein A), such that the complex can be used to determine the presence or absence of PBP2a (or Protein A) in a given sample.

PBP2a-specific antibodies according to the present invention can be antibodies that make specific bindings to a polypeptide comprising PBP2a fragment having the amino acids of SEQ ID NO: 1, which displays low degree of inter-species homology among PBP2a sequences. Preferably, said PBP2a-specific antibodies can be monoclonal antibodies.

In addition, said PBP2a fragment having the amino acids of SEQ ID NO: 1 can be purified from said MRSA strain, or can be prepared in the form of recombinant protein through the use of vector. Preferably said PBP2a fragment can be obtained by vector cloning using EcoR I and Xho I as restriction enzyme.

Said polypeptide is constructed to include the N-terminal region specific to PBP2a of MRSA, which is found so by homology analysis of PBP2a among various strains of *Staphylococcus aureus* (see Example 1-1).

As such, the antibodies according to the present invention can recognize said polypeptide as antigen and thereby detect the presence of PBP2a. Preferably, the antibodies can be monoclonal antibodies. Said monoclonal antibodies can be prepared using conventional antibody preparation techniques. It is preferred that antibodies are produced from a hybridoma selected from the group consisting hybridomas of KCLRF-BP-00202, KCLRF-BP-00203 and KCLRF-BP-00204 (indicated by deposition number). Said hybridomas were deposited with Korean Cell Line Bank at 28 Yongon-dong, Chongno-Gu, Seoul, 110-744, Korea, on Feb. 18, 2009 and allotted receipt numbers KCLRF-BP-00202, KCLRF-BP-00203 and KCLRF-BP-00204.

In one embodiment of the present invention, a mass of antigens can be prepared using PBP2a-specific primers (see Example 1-2). The antigens were then injected intraperitoneally into mice. Subsequently, a selection was made for polyclonal antibody-producing mice in which polyclonal antibodies showed highest antibody titer against PBP2a but low degree of affinity to His-Coagulase (used as negative control) (see Example 1-3). Hybridomas were made by the fusion between the mouse's spleen cells and myeloma cells. PBP2a-specific monoclonal antibodies were produced from the hybridomas (See Example 2)

Since the monoclonal antibodies according to the present inventions exhibit PBP2a-specific recognition, they can detected MRSA and MR-CNS, which are known to have PBP2a.

In one embodiment of the present invention, it was confirmed by ELISA that the monoclonal antibodies according to the present inventions have PBP2a antigen specificity (see Example 3). It was confirmed by immunoblot assay or ELISA, the monoclonal antibodies according to the present inventions can be used to detect MRSA (See Example 4). Further, in one embodiment of the present invention, pairs of monoclonal antibodies were selected from the monoclonal antibodies according to the present inventions, and it was found that MRSA can be detected by sandwich ELISA or immunochromatographic assay with the use of such monoclonal antibody pairs (see Example 5).

The monoclonal antibodies according to the present invention can be, but not limited to, ones that is combined to a detection label capable of producing detectable signals. Such detection label can be one or more selected from the group consisting of enzymes, fluorescent substances, luminescent and radioactive materials. In more detail, the examples of detection label include various enzymes, prosthetic groups, fluorescent materials, luminescent materials, bioluminescent materials radioactive materials.

The detection labels can be coupled or bound to the monoclonal antibodies according to the present inventions, directly or indirectly via a coupler (i.e., linkers known in this field). Examples of suitable enzymes include: horse radish peroxidase, acetylcholinesterase, peroxidase, alkaline phosphatase, β-D-galactosidase, glucose oxidase, malate dehydrogenase, Glucose-6-phosphate dehydrogenase, and invertase. Examples of suitable prosthetic groups include: streptavidin/biotin and avidin/biotin. Examples of suitable fluorescent materials include: umbelliferon. fluorescein, fluorescein isothiocyanate, rhodamine, dichlorotriazinyl amine fluorescein, dansyl chloride, phycoerythrin and phycobiliprotein. Examples of suitable luminescent materials include: luminal, isoluminol, and lucigenin. Examples of suitable bioluminescent materials include: luciferases, luciferin and aequorin. Examples of suitable radioactive materials include: $^{125}I$, $^{131}I$, $^{111}In$, $^{99}Tc$, $^{14}C$, and $^{3}H$.

Hybridoma cell line to be used for the present invention can be hybridoma cells with accession numbers of KCLRF-BP-00202, KCLRF-BP-00203 or KCLRF-BP-00204. The hybridomas cell lines were deposited with Korean Cell Line Bank on Feb. 18, 2009.

Techniques for producing such hybridomas are widely known to those skilled in the art, and it is preferred that hybridomas are prepared by the fusion between antibody-producing cell and immortal cells (e.g., myeloma cells).

In embodiment of the present invention, hybrodomas in which mouse spleen cells and mouse myeloma cells were fused, by which it was confirmed that PBP2a-specific monoclonal antibodies can be produced (See example 2).

A MRSA detection method according to the present invention can be used to detect MRSA by detecting the presence of antigen-antibody complex, in which method PBP2a-specific antibody and Protein A-specific antibody are each contacted with test samples.

Said PBP2a-specific antibody can be an antibody that specifically binds to a polypeptide comprising a PBP2a fragment having the amino acid sequence of SEQ ID NO: 1. Preferably, the PBP2a-specific antibody specifically binding to a polypeptide comprising a PBP2a fragment having the amino acids of SEQ ID NO: 1 is a monoclonal antibody according to the present invention.

Protein A is a protein specifically expressed in *Staphylococcus aureus*, which is expressed specifically in MRSA and MSSA but not in MR-CNS or MS-CNS.

Said Protein A-specific antibody can be, if not necessary, a polyclonal antibody obtained from chicken immunized with Protein A.

A detection method according to the present invention enables the detection of MRSA by using both a PBP2a-specific antibody and a Protein A-specific antibody. Since Protein A is present in MRSA but is lacking in MR-CNS, the two strains cannot be distinguished with the only use of PBP2a-specific antibody, but can be easily distinguished by using both a PBP2a-specific antibody and a Protein A-specific antibody.

Due to its affinity for the Fc region in many antibodies, Protein A has a difficulty in being detected of Protein A by using antibodies. It is known, however, that anti-Protein A antibody from chicken exhibits no such binding property to Protein A (Larsson A, Sjöquist J. 1989; 27(12):2856-7. J Clin Microbiol.). Therefore, anti-Protein A antibody was prepared by immunizing chickens with Protein A (see Example 6-1)

In one embodiment of the present invention, it was confirmed that MRSA and MSSA, the strains producing Protein A, can be detected by sandwich ELISA or immunochromatographic assay with the Protein A-specific antibody prepared as above (see Examples 6-2 and 6-3).

Therefore, a MRSA detection method of the present invention (1) detects PBP2a by a PBP2a-specific antibody and (2) detects Protein A by a Protein A-specific antibody, thereby enabling the specific detection of MRSA, which has both PBP2a and Protein A. In other words, one can conclude that MRSA exists when positive antigen-antibody reactions are observed in both detections of (1) and (2).

In one embodiment of the present invention, the presence of MRSA was detected through the antigen-antibody reactions of (1) and (2) as explained above. See Example 7.

Methods to check the presence of said antigen-antibody complex include, but are not limited to: radioactivity immunoanalysis, ELISA (enzyme-linked immunosorbent assay), sandwich immunoanalysis, and lateral flow immunographic assay. Detection of antigen-antibody complexes involves the use of an antibody labeled directly or indirectly. A usable detection label is described above. The methods are widely known to those skilled in the art. For instance, in case of ELISA, test samples are contacted with the monoclonal antibody according to the present invention or with a Protein A-specific antibody, as coated on microtiter plates, membranes, test strips, and the likes. In one embodiment, microtiter plate wells can be coated with the monoclonal antibodies according to the present invention or with a Protein A-specific antibody, and non-occupied binding sites are blocked with BSA. The coated wells are incubated with test samples, and are examined to see the presence of antigen-antibody complexes. The antibodies can be labeled for detection as described above.

Figure 8A:
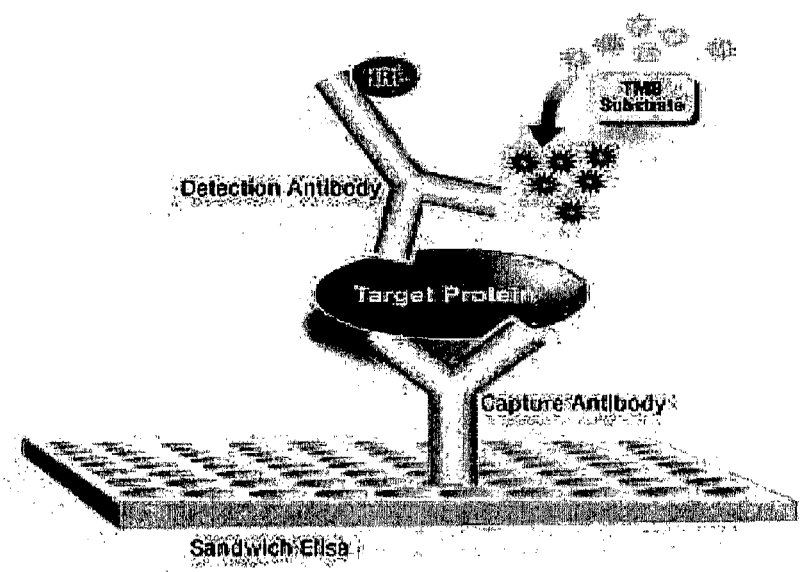
FIG. 8a is a brief operation concept for sandwich ELISA.
Figure 8B:
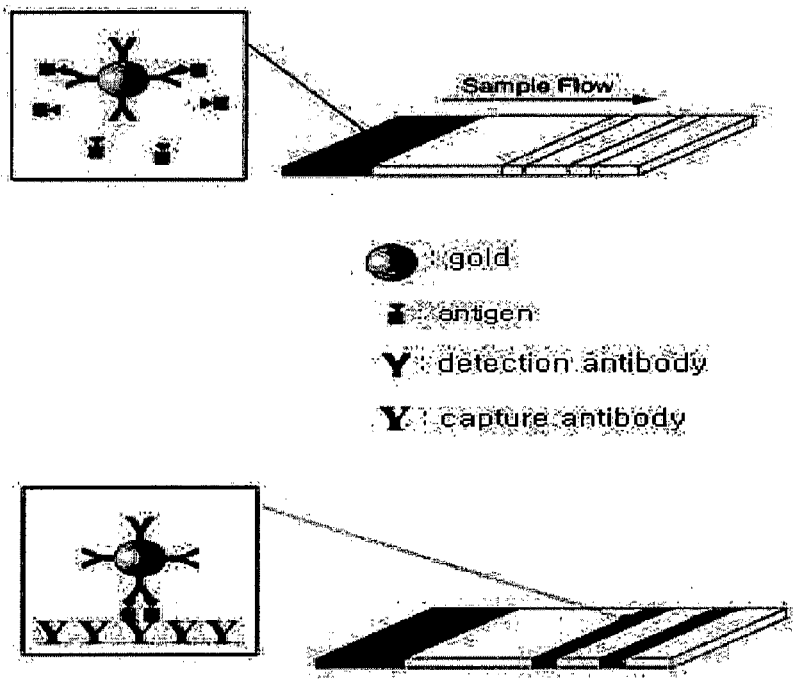
FIG. 8b is a brief operation concept for (rapid) lateral flow immunographic assay.

Particularly where sandwich immunoanalysis and lateral flow immunographic assay are used, MRSA detection can be conducted by using antibody pairs as prepared from the monoclonal antibodies according to the present invention. See FIG. 8. Such antibody pairs can be any ones that employ one of the monoclonal antibodies according to the present invention. It is preferred that the monoclonal antibody produced from the KCLRF-BP-00202 hybridoma is used as detection antibody, with the monoclonal antibody produced from KCLRF-BP-00203 or KCLRF-BP-00204 hybridoma used as coating antibody.

In one embodiment of the present invention, MRSA detection could be achieved through sandwich immunoanalysis and lateral flow immunographic assay, by selecting monoclonal antibody pairs and by using the same. Particularly, an effective detection of MRSA was performed where the monoclonal antibody produced from the KCLRF-BP-00202 hybridoma was used as detection antibody, with the monoclonal antibody produced from KCLRF-BP-00203 or KCLRF-BP-00204 hybridoma used as coating antibody. See Example 5.

A MRSA detection kit according to the present invention contains a PBP2a-specific antibody and a Protein A-specific antibody.

Said PBP2a-specific antibody can be an antibody that makes a specific binding to a polypeptide comprising a PBP2a fragment having the amino acids of SEQ ID NO: 1. Preferably, said PBP2a-specific antibody is the monoclonal antibody according to the present invention.

Said kit systems that can be used for the present invention include, but are not limited to: ELISA plates, a deep-stick device, an immunochromatographic assay, radial partition immunoassay device, a flow-through device, etc. Preferably, a diagnostic kit provided in immunochromatographic strip or device form can be used. In immunochromatographic diagnosis, antigens contained in testing serum react with tracer antibody bound to colloidal gold particle. Then while migrating through micropores on the nitrocellulose membrane by capillary action, the antigens are bound to capture antibody to produce color development on the strip, such that positive and negative signals are observable by naked eye.

Such kit can preferably employ ELISA or lateral flow immunographic assay. As stated previously, antibody pairs prepared using the monoclonal antibodies according to the present invention can be used for MRSA detection when sandwich immunoassay and lateral flow immunographic assay are used.

A kit that can be used for the present invention can be, but is not limited to, one comprising: solid phase support; the monoclonal antibodies according to the present invention and a Protein A-specific antibody; and ELISA reaction fluids containing enzyme-labeled antibody solution for reacting with antigen and a dye reagent for signaling enzyme reaction. In more detail, said enzyme-labeled antibody solution can be of goat anti-mouse Ig-HRP (50-150 μl per well at appropriate concentrations). The dye reagent can be selected from the group consisting of tetramethylbenzidines (TMB). Stopping solution can be selected from the group consisting of 1N HCl and 1N $H_2SO_4$.

A composition for MRSA detection according to the present invention comprises a PBP2a-specific antibody and a Protein A-specific antibody.

Said PBP2a-specific antibody can be an antibody that makes a specific binding to a polypeptide comprising a PBP2a fragment having the amino acids of SEQ ID NO: 1. Preferably, said PBP2a-specific antibody can be the monoclonal antibody according to the present invention.

Said composition may further include a carrier used for immunoassay, a detection label capable of producing detectable signals, a resolvent, and a cleaner, in addition to said PBP2a-specific antibody and Protein A-specific antibody. In addition, in the case where labeling substance is an enzyme, the composition may further include substrates and a reaction stopper. Examples of a suitable carrier include, but are not limited to, soluble carriers, for example, physiologically acceptable buffer solution known in the art (e.g., PBS), insoluble carriers, for example, polystyrene, polyethylene, polypropylene, polyester, polyacrylonitrile, fluorine resin, crosslinked dextran, polysaccharides, macromolecules including magnetic microparticle of metal plated on latex, paper, glass, metal, agarose, and combinations thereof.

As explained above, the present invention enables a fast and accurate detection of MRSA, which has both PBP2a and Protein A, by using a PBP2a-specific antibody for the detection of PBP2a and using a Protein A-specific antibody for the detection of Protein A.

The present invention is further explained in more detail with reference to the following examples. These examples, however, should not be interpreted as limiting the scope of the present invention in any manner.

EXAMPLE 1

Preparation of Polyclonal Antibodies Specific to PBP2a in MRSA

<1-1> Determination of Specific Sites in PBP2a

SIB BLAST NetworkService (ExPASy Proteomics Server, http://au.expasy.org/tools/blast/) was used to measure the interspecies homology for PBP2a of *Staphylococcus aureus*. The result is as shown in FIG. 1.

Figure 1B:
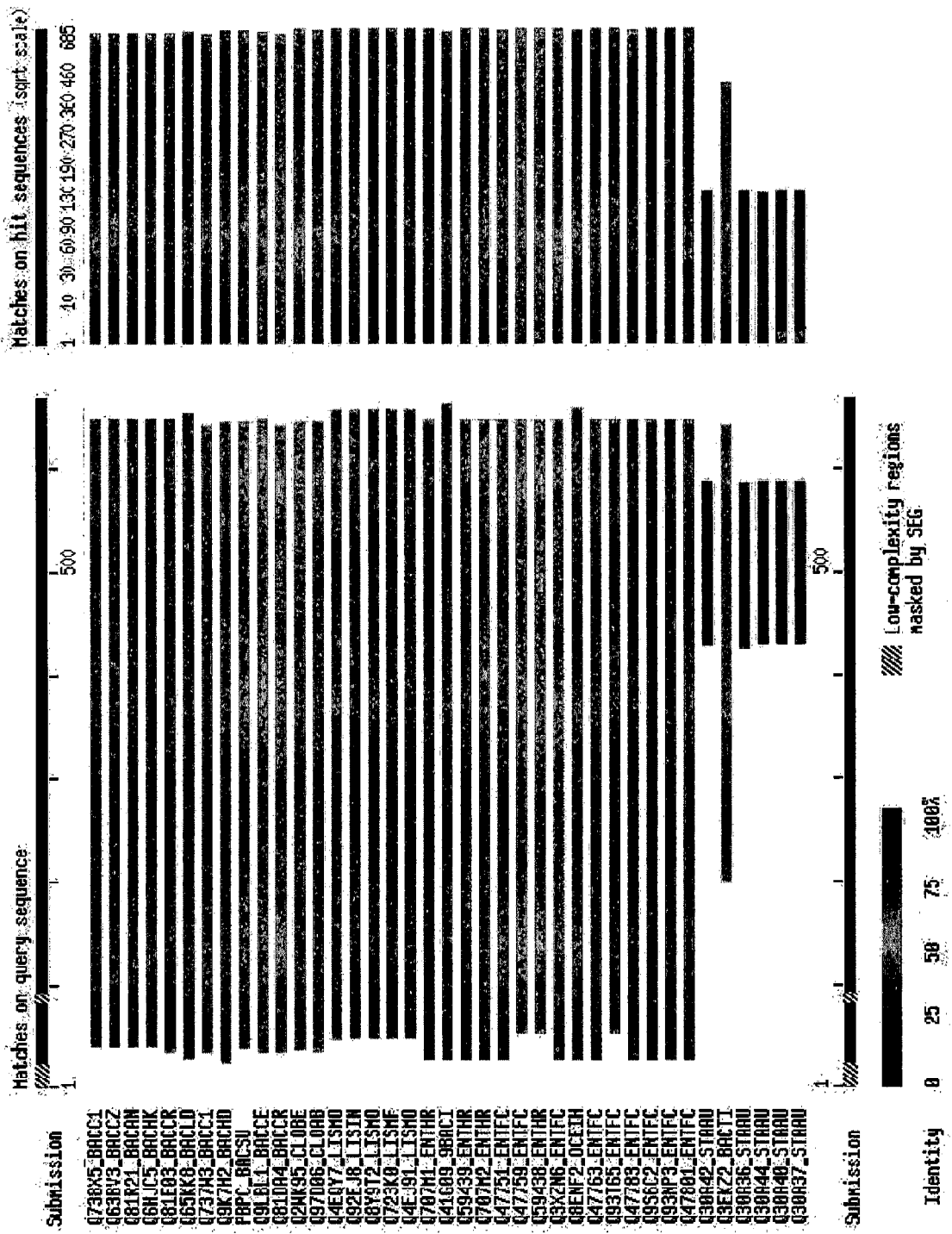
Figure 1C:
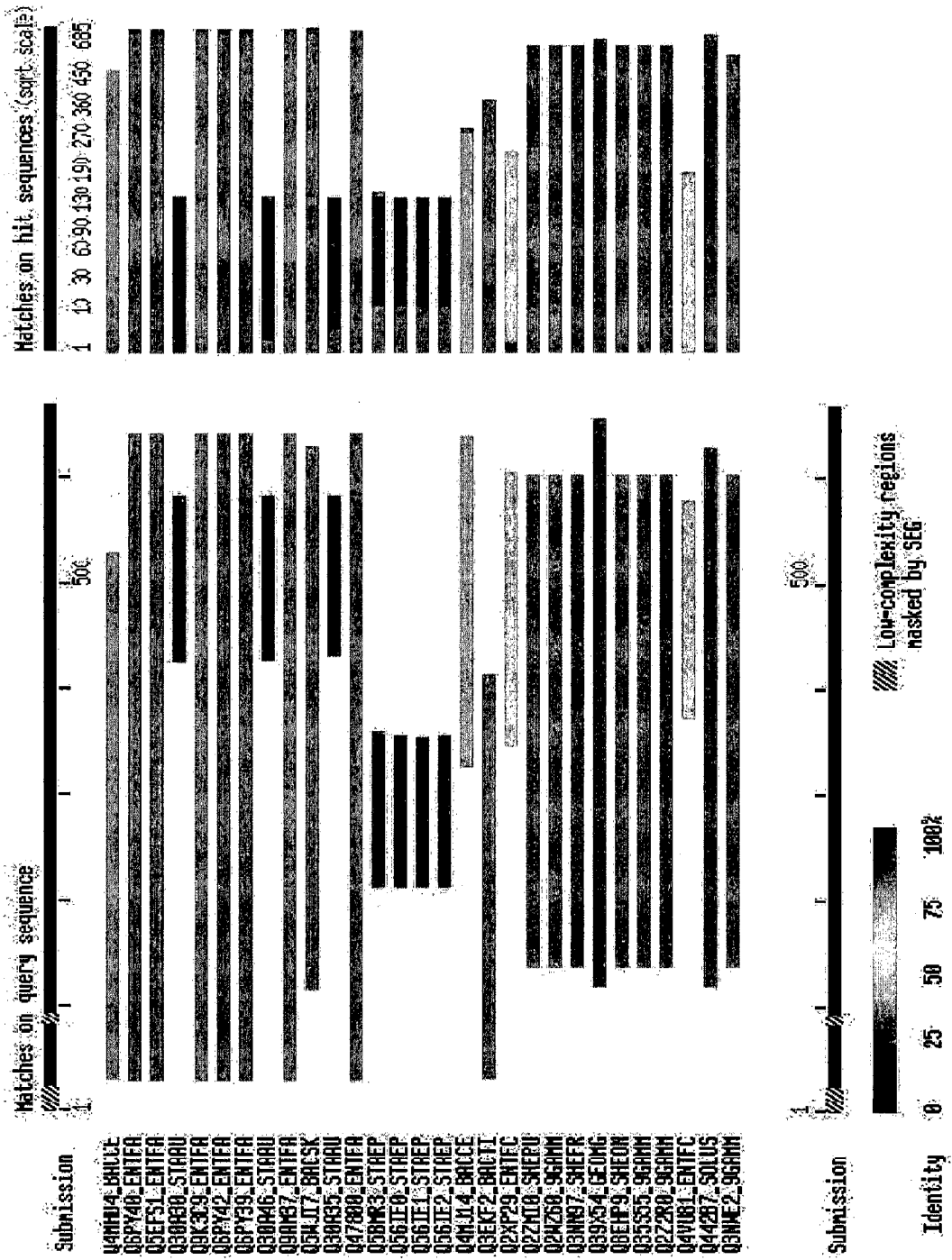

In FIG. 1*a* to 1*c*, green indicates high homology, and all parts indicated green were from bacteria having PBP2a. For the bacteria having PBP2a, SIB BLAST NetworkService (ExPASy Proteomics Server, http://au.expasy.org/tools/blast/) was used to determine sequence groups showing low homology.

As shown in FIG. 2, N-terminal showed low homology, while C-terminal showed relatively high homology. In addition, at the C-terminal part, which relates to functioning of transpeptidase a high degree of homology among similar PBP2a was observed. As such, N-terminal part (SEQ ID No: 1) was chosen as a MRSA-specific site in PBP2a protein. The whole amino acid sequence for PBP2a is as provided in SEQ ID No: 2

<1-2> PBP2 Antigens

PCR was performed on the gene DNA extracted from colonies of MRSA under the condition presented in the Table 1. The PBP2a-specific primers in Table 2 below were used.

TABLE 1

| PCR Condition | | |
|---|---|---|
| | Reaction Temperature and Duration | Number of Cycles |
| Denature | 95° C. 7 min | |
| Cycles | 95° C. 30 s | 30 cycles |
| | 58° C. 30 s | |
| | 72° C. 1 min 30 s | |
| Elongate | 72° C. 7 min | |

TABLE 2

PBP2a-specific primers

| Sense | SEQ ID NO. 3 | 5'-GGAATTCGGTATATATTTTTATGCTTC-3' |
|---|---|---|
| Anti-sense | SEQ ID NO. 4 | 5'-TCTCGAGAGTACCTGAGCCATAATC-3' |

Figure 3:
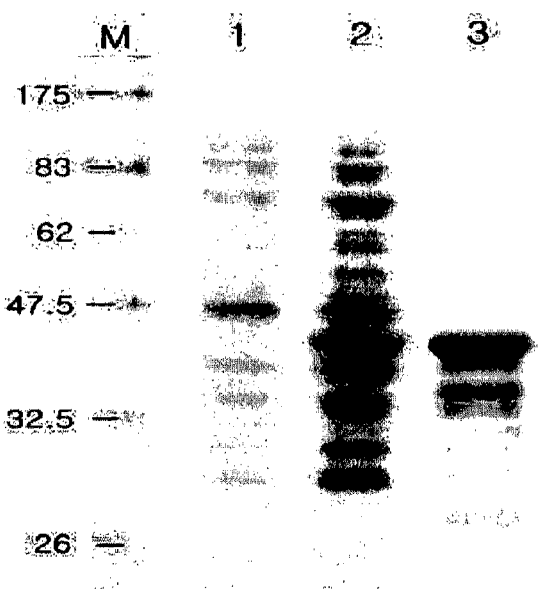
FIG. 3 shows the results of electrophoresis of polypeptides expressed in bacteria, where the polypeptides were obtained by using PBP2a-specific primers, according to an embodiment of the present invention. On the gel, line M shows the markers for molecular mass of 175 kDa, 83 kDa, 62 kDa, 47.5 kDa, 32.5 kDa, and 26 kDa, respectively. Line 1 is for pre-protein expression, Line 2 is for expression of 37 kDa His-PBP2a, and Line 3 is for protein obtained after purification.

Resultant PCR products of 988 bp bases were cloned into pET vector using the restriction enzymes of EcoR I and Xho I, and PBP2a protein was then expressed. PBP2a protein was observed on electrophoresis, the result of which is shown in FIG. 3. FIG. 3 shows that about 37 kDA protein was produced with the use of the PBP2a-specific primers.

<1-3> Preparation of Polyclonal Antibody Against PBP2a

The PBP2a recombinant protein from Example 1-1 was injected intraperitoneally to female BALB/c mice at 6 wk (50 µg injection per mouse). With Freund's adjuvant used, the mice were immunized three times with one month interval. Then the blood was collected from the tails and was centrifuged for 2-3 minutes at 14,000 rpm to obtain the serum in the supernatant. Polyclonal antibodies including anti-PBP2a antibodies were obtained in the serum.

Antibody titer of said polyclonal antibodies was measured by an indirect ELISA in which the wells were coated with the recombinant antigen. The results are shown in Tables 3 and 4, and in FIG. 4. His-Coagulase was used as control in order to obtain a better determination of antibody titer against PBP2a, not against His.

TABLE 3

Antibody titer against His-PBP2a in polyclonal antibodies

| Serum dilutions | His-PBP2a 10 ng/well | | | | |
|---|---|---|---|---|---|
| | #1 mouse | #2 mouse | #3 mouse | #4 mouse | #5 mouse |
| 1/1,000 | 0.883 | 1.339 | 1.376 | 1.711 | 1.150 |
| 1/10,000 | 1.695 | 1.705 | 1.965 | 1.892 | 1.878 |
| 1/100,000 | 0.964 | 0.640 | 0.879 | 0.511 | 0.997 |
| 1/1,000,000 | 0.123 | 0.061 | 0.162 | 0.222 | 0.143 |

TABLE 4

Antibody titer of polyclonal antibodies against His-Coagulse

| Serum dilutions | His-Coagulse 10 ng/well | | | | |
|---|---|---|---|---|---|
| | #1 mouse | #2 mouse | #3 mouse | #4 mouse | #5 mouse |
| 1/1,000 | 0.285 | 0.481 | 0.741 | 0.553 | 1.235 |
| 1/10,000 | 0.007 | 0.067 | 0.047 | 0.012 | 0.061 |
| 1/100,000 | 0.000 | 0.008 | 0.006 | 0.002 | 0.004 |
| 1/1,000,000 | −0.001 | 0.000 | −0.003 | −0.002 | −0.002 |

Figure 4:
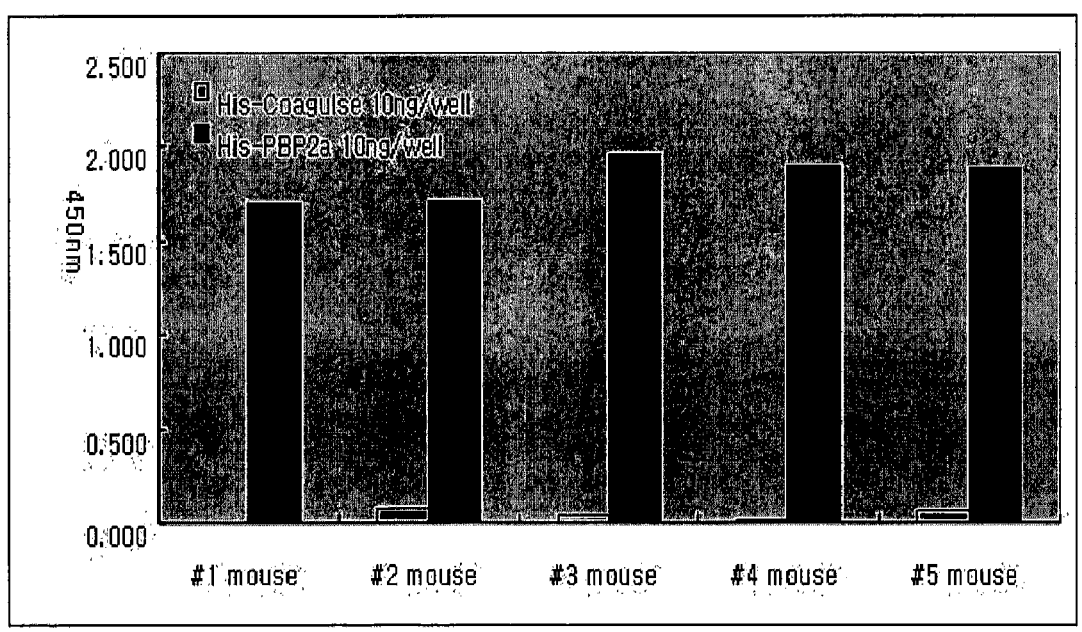
FIG. 4 shows an ELISA analysis result in which formation of His-PBP2a specific antibody is shown, with comparison to His-Coagulase (negative control antigen), according to an embodiment of the present invention.

As shown in Tables 3 and 4, and FIG. 4, the highest antibody titer was from #3 mouse among the five mice. Antibodies that bind to His-PBP2a showed high affinity to His-PBP2a but low affinity to His-Coagulase, the negative control antigen.

EXAMPLE 2

Preparation of Monoclonal Antibodies Specific to PBP2 of MRSA

<2-1> Preparation of Hybridomas

Hybridoma cells, which produced monoclonal antibodies, were produced from the #3 mouse in Example 1-3, which showed the highest polyclonal antibody titer against the PBP2a. Specifically, the spleen was harvested to obtain a single cell suspension. The suspension was washed with RPMI 1640 (Hyclone) at two times, and cell counting was carried out by tryphan blue staining.

As the cells to be fused with the spleen cells, SP2/0 or X63 mouse myeloma cell line (ATCC CRL-1581, ATCC CRL-1580) was used. As conducted with the spleen cells, washing and cell counting were carried out with the myeloma cells. After centrifuging a mixture of the spleen cells and the myeloma cells (at a 1:5 ratio of the spleen cells to the myeloma cells), the supernatant was removed. 1500 ml of preheated (37° C.) 50% polyethylenglycol was added gradually for one minute. The sample was placed at rest for one minute. Then a serial dilution was made with the addition of RPMI-1640 (Hyclone). The sample was subsequently centrifuged and suspended in RPMI 1640 (20% FBS, hypoxanthine-aminopterin-thymidine) containing 1×HAT. The solution was plated in 96 well plates (100 µl per well), which were then incubated at 37° C. in the 5% $CO_2$ incubator.

<2-2> Separation and Selection of Hybridomas

After HAT feeding was carried out with the hybridomas (the myeloma cells fused with the spleen cells, from Example 2-1), upon appearance of colonies in the wells, 200 ul supernatant was collected. Monoclonal antibodies were selected by ELISA.

Specifically, for the selection of monoclonal antibodies, ELISA plates were coated with recombinant PBP2a protein (100 ng per well), into which 100 ul of the above supernatant was then added. ELISA was performed with goat anti-mouse Ig-HRP.

After antibody-positive hybridomas were screened by ELISA, those hybridomas were moved into and cultured in 24 well-plates containing HFCS (Hybridoma fusion and cloning supplement, Roche). Once the colonies take approximately 50-70% of the plates, antibody-positive hybridomas were again screened, and the selected hybridomas were cloned (single cell cloning) by limiting dilution. The hybridomas were expanded to the last clone which was shown to produce antibodies, such that three hybridomas were prepared that produce monoclonal antibodies against PBP2a-antigens, as shown in Table 5.

TABLE 5 hybridomas that produce monoclonal antibodies against PBP2a-antigens

| Clone # | |
|---|---|
| 1 | 6G10-46-63 |
| 2 | 9C6-52-40 |
| 3 | 17A10-2-2 |

The hybridomas were deposited with Korean Cell Line Bank on Feb. 18, 2009, and received as accession number of KCLRF-BP-00202 for the clone 6G10-46-63; accession number of KCLRF-BP-00203 for the clone 9C6-52-40; and accession number KCLRF-BP-00204 for the clone 17A10-2-2.

<2-3> Isolation and Purification of Monoclonal Antibodies

Procedures were carried out for mass purification of hybridoma clones obtained from Example 2-2. 0.5 ml of incomplete Freund's adjuvant was intraperitoneally injected, and 10 days later, $5 \times 10^6$ hybridoma cells were injected into the intraperitoneal cavity as suspended in 0.5 ml of PBS.

Ascites fluids were collected from the intraperitoneal cavity between 10 and 14 days following the injection of hybridomas and were centrifuged. 0.02% sodium azide was added as a conservative. Monoclonal antibodies were purified using Protein A or G sepharose beads, depending on the isotypes of the antibodies. The obtained monoclonal antibodies for the three different clones were labeled: '6G10', '9C6' and '17A10', respectively.

EXAMPLE 3

ELISA Verification of Antigen-Specificity of the Monoclonal Antibodies

<3-1> ELISA Determination of PBP2a Antigen-specificity of the Monoclonal Antibodies ELISA plates (Maxisorp, Nunc) were incubated for coating with His-PBP2a, which were added in serial dilutions by PBS (initially at 10 ng/well), for one hour after each dilution at 37° C. The plates were further incubated for extra one hour at 37° C. in 3% BSA/PBS for blocking.

Monoclonal antibodies from Example 2-3, after being diluted with PBS, were placed in the wells (1 ug per well) and were incubated for one hour to allow for antigen-antibody reaction. The wells were then washed three times. After Ig-HRP (Horse radish peroxidase, Dinona) being treated on the antibodies bound, the wells were incubated for 30 min at 37° C.

Figure 5A:
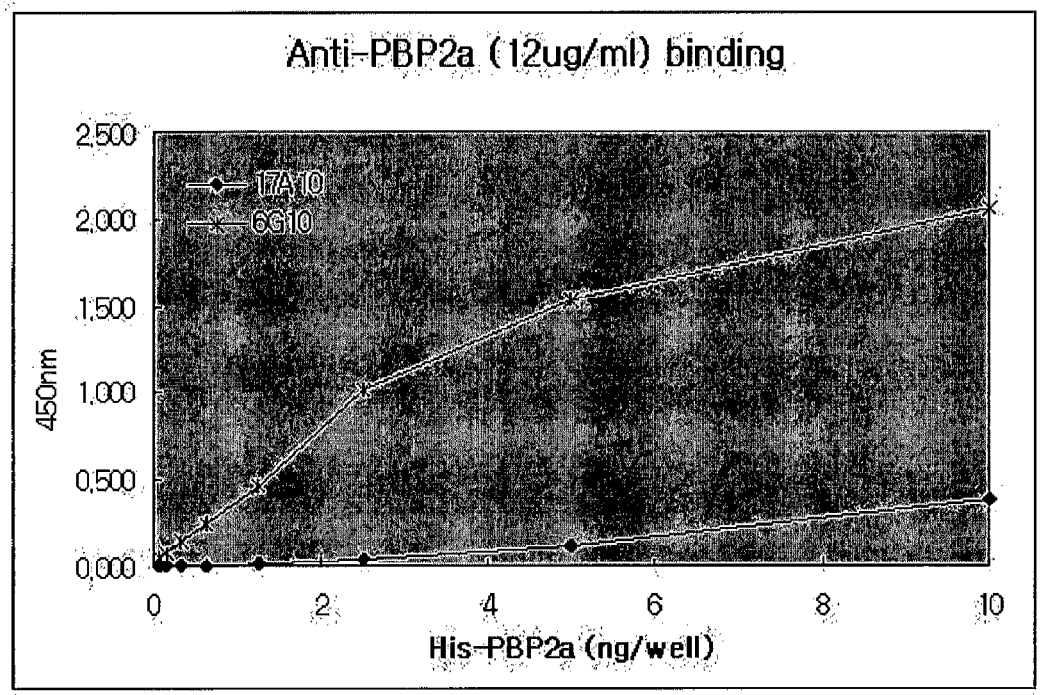
FIGS. 5a and 5b show degrees of affinity to His-PBP2a as exhibited by the monoclonal antibodies according to the present invention. Specifically.
Figure 5B:
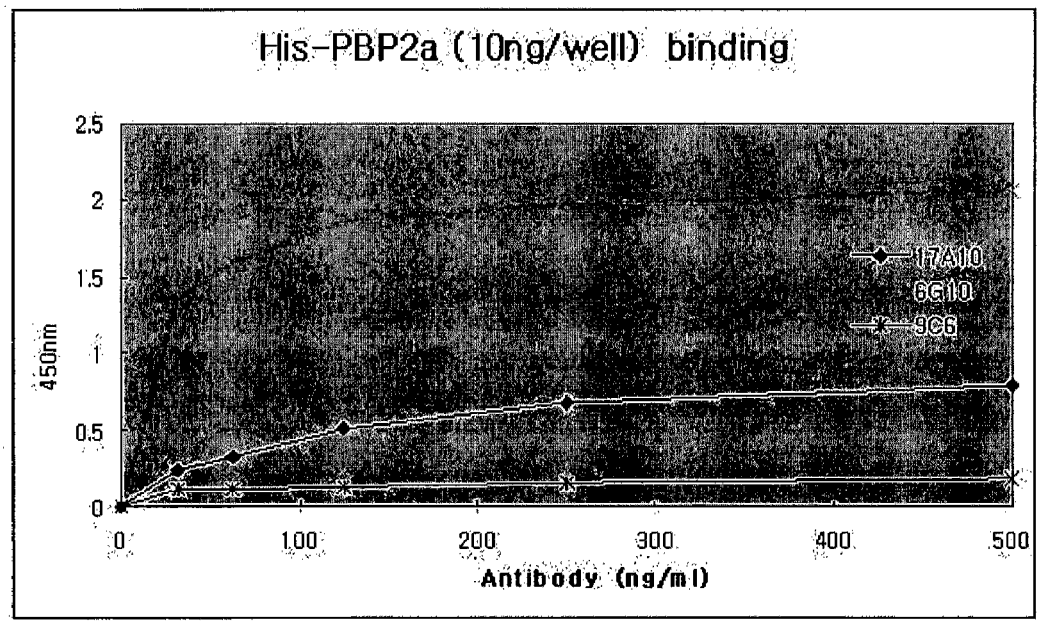

After the incubation, the wells were washed three times again. The wells were treated with TMB solution (50 ul per well) as substrate for color reaction and then were allowed for color reaction for 10 min. The reaction was stopped with the addition of stop solution (50 ul per well). The intensity of the color development was measured at 450 nm for the monoclonal antibodies prepared according to the embodiments of the present invention. The result is as shown in FIG. 5a. FIG. 5b shows the result where the wells were coated with His-PBP2a (10 ng per well), with antibody added in serial dilutions (initially at 500 ng/ml).

As seen in FIGS. 5a and 5b, respective monoclonal antibodies showed different degrees of bindings to antigen.

<3-2> ELISA Determination of Protein A Antigen-specificity of the Monoclonal Antibodies Protein A, a protein specific to *Staphylococcus aureus*, is known to make a binding to the Fc region of antibodies (Larsson A, Sjöquist J. 1989; 27(12):2856-7. J Clin Microbiol./Lindmark R, Sjöquist J. 1983; 62:1-13. J. Immunol. Methods). Therefore, using antibodies with low affinity to Protein A can increase PBP2a specificity of the antibodies. In this connection, the present inventors examined the degrees by ELISA in which the monoclonal antibodies as prepared in the Example 2-3 bind to Protein A.

Protein A (Fluka Inc.) from *Staphylococcus aureus* was added in serial dilutions by PBS (initially at 100 ng/well) into Maxisorp plates (Nunc.), which were then incubated for coating for one hour after each dilution at 37° C. Subsequently the wells were incubated for another hour in 3% BSA/PBS at 37° C. for blocking. Into the wells prepared as such, the monoclonal antibodies obtained from Example 2-3 were added at 1 ug/well after being diluted. The wells were incubated for one hour such that antigen-antibody reaction was induced, and then were washed three times. After being treated with Ig-HRP (Horse radish peroxidase, Dinona) on the antibodies bound, the wells were incubated for 30 min at 37° C. The wells were then treated with TMB solution (50 ul per well) as substrate for color reaction and were allowed for reaction for 10 min. The reaction was stopped with addition of stop solution (50 ul per well). The intensity of the color development was measured at 450 nm for the monoclonal antibodies prepared according to the embodiments of the present invention. The result is as shown in FIG. 6.

Figure 6:
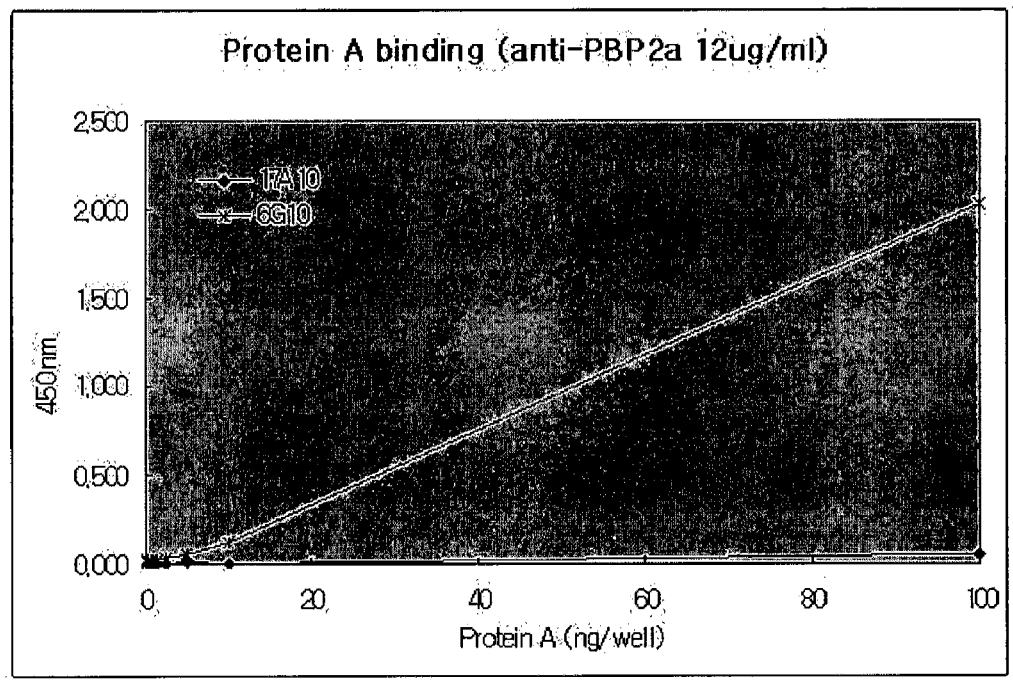
FIG. 6 is the graph showing the ELISA result where affinity to Protein A was assayed as exhibited by the monoclonal antibodies of the present invention, according to an embodiment of the present invention.

FIG. 6 showed that respective monoclonal antibodies showed different degrees of specificity to Protein A, indicating that immunoassay using the monoclonal antibodies according to the embodiments of the present invention could be conducted without being affected by Protein A.

EXAMPLE 4

MRSA Detection

<4-1> Isolation of Cell Lysates from Bacteria of MRSA Group

For the present example, bacterial strains isolated/identified by Chungbuk National University Hospital were provided. The bacteria were washed with PBS two times, and were cultivated for 30 min as suspended in the bacterial lysis buffer (B-PER buffer, Pierce). Subsequently, a freezing-thawing procedure was performed two times at −70° C. The cells were then centrifuged at 14,000 rpm for 25 min. Lysates from each bacterial line were obtained from the supernatant collected after the centrifugation. Bradford assay was performed to quantify protein level, and the result of which is shown in Table 6 below.

TABLE 6

Absorptions and concentrations of bacterial lysates

| | 562 nm absorption | | concentration (ug/ml) | | |
|---|---|---|---|---|---|
| | Undiluted | diluted ½ | Undiluted | diluted ½ | Average |
| MSSA 1765 | 1.083 | 0.857 | 445 | 325 | 385 |
| MSSA 1886 | 1.528 | 1.077 | 1001 | 875 | 938 |
| MRSA 80 | 2.009 | 1.382 | 1602 | 1637 | 1620 |
| MRSA 85 | 1.951 | 1.351 | 1530 | 1560 | 1545 |
| MRSA 97 | 1.317 | 1.051 | 737 | 810 | 774 |
| MRSA 361 | 2.152 | 1.689 | 1781 | 2405 | 2093 |
| MRSA 1395 | 1.353 | 1.079 | 782 | 880 | 831 |
| MRSA 1672 | 1.962 | 1.430 | 1544 | 1757 | 1650 |
| MRCNS 204 | 1.577 | 1.223 | 1062 | 1240 | 1151 |
| MSCNS 6535 | 1.674 | 1.224 | 1184 | 1242 | 1213 |

<4-2> MRSA Detection with Immunoblot Assay

Immunoblot assay was performed to test whether the monoclonal antibodies obtained from Example 2-3 can be used to detect PBP2a in MRSA, MSSA and MS-CNS.

Detailed explanations are as follows. Lysate proteins of *Staphylococcus aureus* were run on 10% SDS-PAGE (1 ug/lane) and were electro-transferred to nitrocellulose membranes. Subsequently one hour of cultivation in 5% BSA/PBS at room temperature was made to stop reactions at protein-absent areas. With the addition of the monoclonal antibodies from Example 2-3, as diluted with PBS (1 ug/ml), the membranes were further incubated for one hour to induce antigen-antibody reactions, and were subsequently washed three times. After being treated with Ig-HRP (Horse radish peroxidase, Dinona) on the antibodies bound, the membranes were incubated for 30 min at 37° C. and were washed three times. After being treated with ECL (enhanced chemiluminescence, PIERCE) for reaction enzyme, the membranes were exposed to an X-ray film. The result is as shown in FIG. 7a.

Figure 7A:
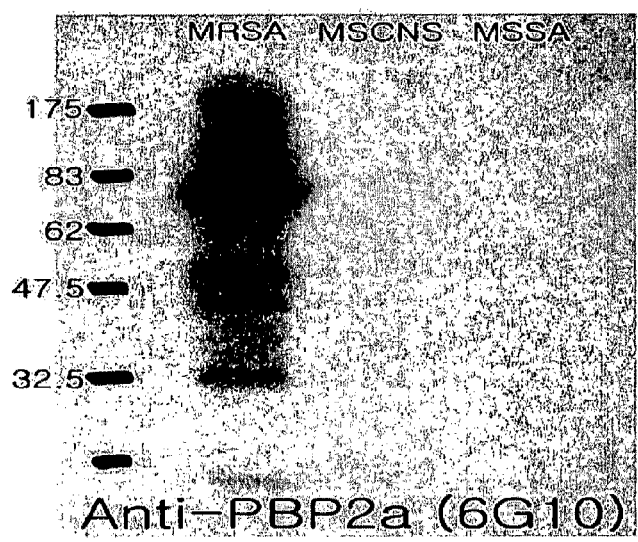
FIGS. 7a and 7b shows the presence of PBP2a as examined in MRSA, MSSA, and MS-CNS, using the monoclonal antibodies of the present invention. Specifically.

As shown in FIG. 7a, about 70 kDa PBP2a appeared in only MRSA, which suggested that MRSA could be detected effectively using the monoclonal antibodies prepared according to the embodiments of the present invention.

<4-3> MRSA Detection with ELISA Assay

ELISA plates (Maxisorp, Nunc) were incubated for coating with MRSA lysates, which were added in serial dilutions with PBS (initially at 10 ng/well), for one hour after each dilution at 37° C. The plates were further incubated for one hour at 37° C. in 3% BSA/PBS for blocking. The monoclonal antibodies from Example 2-3, after being diluted with PBS, were placed in the wells (1 ug per well) and were incubated for one hour in order for antigen-antibody reaction to be allowed.

The wells were then washed three times. After treatment with Ig-HRP (Horse radish peroxidase, Dinona) on the antibodies bound, the wells were incubated for 30 min at 37° C. C. After the incubation, the wells were again washed three times. The wells were treated with TMB solution (50 ul per well) as substrate for color reaction and were allowed for reaction for 10 min. The reaction was stopped with addition of stop solution (50 ul per well). The intensity of the color reaction was measured at 450 nm. The result is as shown in FIG. 7b.

Figure 7B:
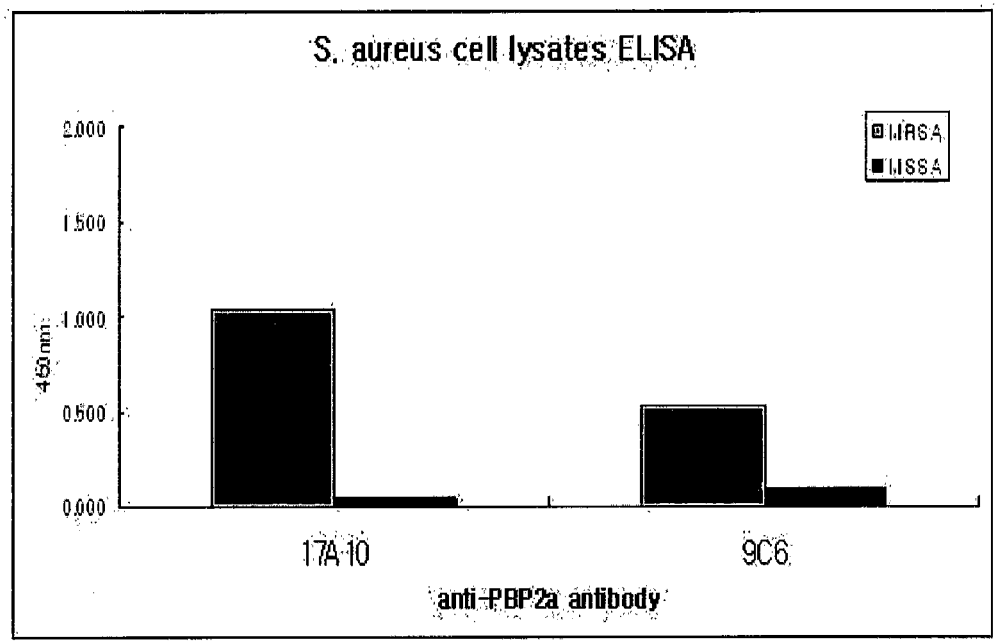

FIG. 7b showed that the monoclonal antibodies obtained from Example 2-3 exhibited higher affinity to MRSA, than to MSSA, although differences existed among the monoclonal antibodies.

EXAMPLE 5

MRSA Detection Using a Pair of Antibodies
<5-1> Selection of a Pair of Monoclonal Antibodies
In order to apply antibodies to immunoassays such as sandwich ELISA and rapid kit, antibodies must recognize a given antigen in pairs (not by single antibodies) (After R. A. Goldsby, T. J. Kindt, B. A. Osborne, Kuby Immunology, 4th ed. (W. H. Freeman and Company, 2000), p. 162) (see FIGS. 8a and 8b).

To determine the most appropriate pair of antibodies to recognize PBP2a antigen, the monoclonal antibodies obtained in Example 2-3 were diluted with PBS as capture antibody (100 ng per a well), incubated one hour at 37° C. and coated on Maxisorp plate. Then, the wells were incubated in 3% BSA/PBS for one hour and blocked. His-PBP2a in serial dilutions with PBS were added into the wells at an amount of 10 ng/well, incubated for one hour at 37° C. and then bounded to the coated antibodies.

After the wells were washed three times, the monoclonal antibodies bound by biotin were diluted 1:1000 with PBS, added into the wells at an amount of 100 ul/well, incubated for one hour to allow bindings with the antigen.

After washing the plate at three times, the antigen-antibody complexes were incubated for 30 min at 37° C. with the treatment of Streptavidin-Horse radish peroxidase (HRP). After washing three times again, the wells were treated with TMB solution (50 ul per well) as substrate for reaction enzyme, and substrate-enzyme reaction was allowed for 10 min. The reaction was stopped with addition of stop solution (50 ul per well). The intensity of the color reaction was measured at 450 nm. The result was shown in FIG. 9a.

Figure 9A:
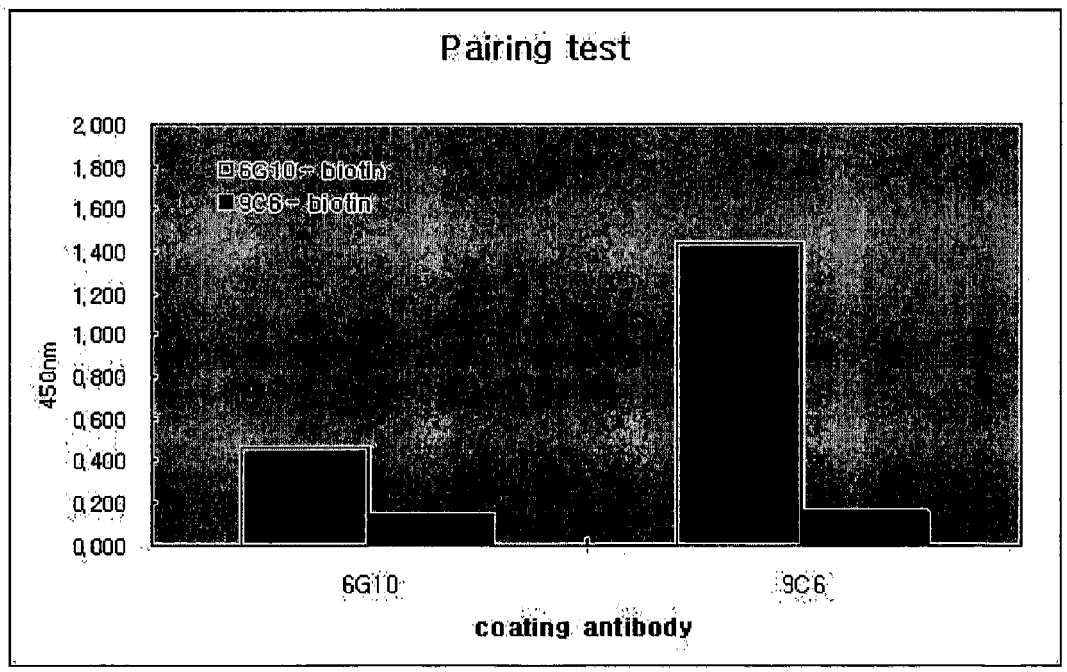
FIGS. 9a to 9c show that PBP2a antigen can be detected by preparing pairs of coating and detection antibodies from the monoclonal antibodies of the present invention; and by using such pairs. Specifically.

FIG. 9a showed that an antibody pair from monoclonal antibodies obtained from Example 2-3 could effectively recognize PBP2a antigen. Particularly, detection efficiency for a given identical concentration of His-PBP2a was highest when 6G10 monoclonal antibody was used for detection along with 9C6 monoclonal antibody for coating.

Figure 9B:
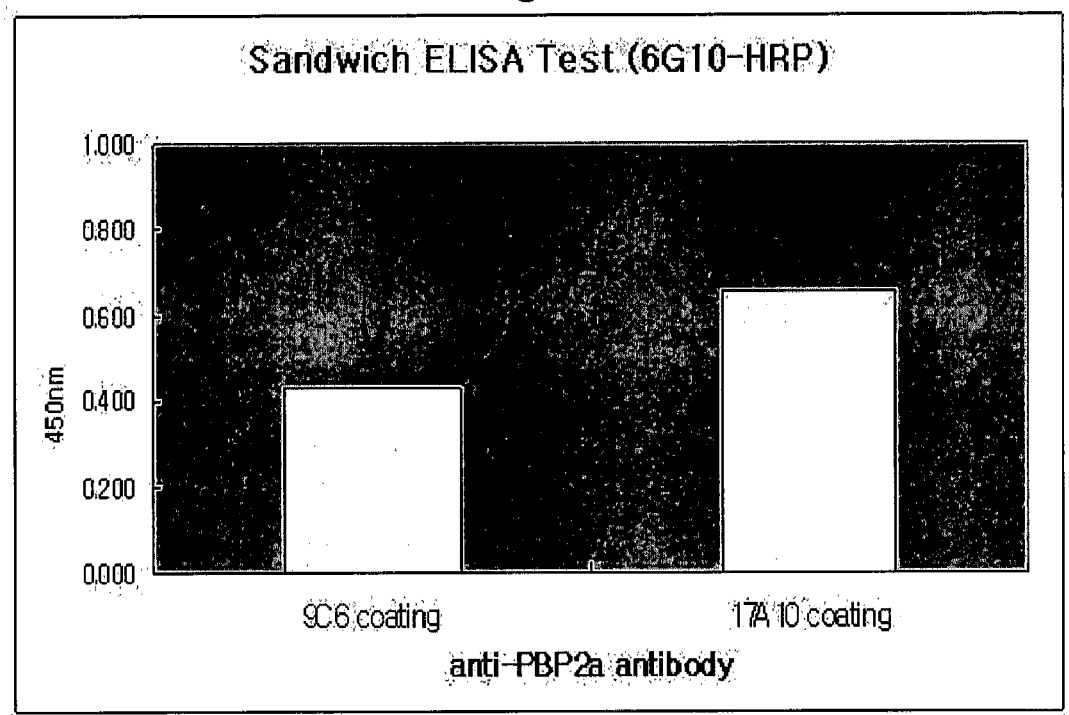

FIG. 9b showed differences in affinity to His-PBP2a according to kinds of antibodies used for coating when 6G10 monoclonal antibody, without being bound to HRP for detection purposes.

FIG. 9b indicated that antibody pairs exhibited differences in affinity to a given (same) concentration of His-PBP2a, but that the monoclonal antibodies according to the present invention were capable of effectively recognizing PBP2a antigen.

Figure 9C:
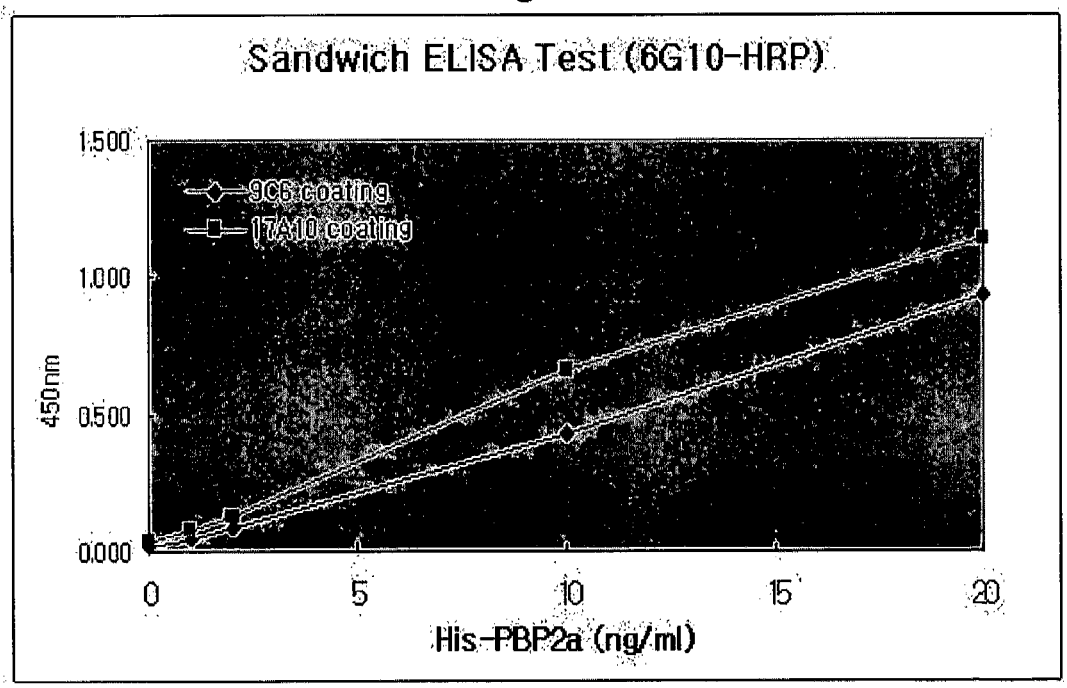

FIG. 9c showed changes in binding affinity of the antibody pairs, after each serial dilution of His-PBP2a.

FIG. 9c indicated that differences in binding affinity were observed in the antibody pairs after serial dilutions but that the monoclonal antibodies according to the present invention were capable of effectively recognizing PBP2a antigen.

<5-2> MRSA Detection with Sandwich ELISA Assay Using Antibody Pairs

Maxisorp plates (Nunc.) were incubated for coating with the monoclonal antibodies as capture antibody in serial dilutions with PBS (initially 100 ng/well) for one hour after each dilution at 37° C. The plates were further incubated for one hour at 37° C. in 3% BSA/PBS for blocking. The lysates of MRSA and MSSA from Example 4-1, serially diluted in PBS, were added into the wells (initially 100 ng/well) and were incubated for one hour after each dilution at 37° C. for their bindings with the coated antibodies.

After three-times of washing, '6G10' monoclonal antibody obtained from Example 2-3 was bound to HRP (Horse radish peroxidase). Then the antibody was added as diluted 1:1000 with PBS into the wells (100 ul/well), and the wells were incubated for one hour for antibody-antigen binding.

After three-times of washing again, the wells were treated with TMB solution (50 ul per well) as substrate for color reaction for 10 min. Then substrate-enzyme reaction was allowed for 10 min. The reaction was stopped with addition of stop solution (50 ul per well). The intensity of the color reaction was measured at 450 nm. The result is as shown in FIG. 10a.

Figure 10A:
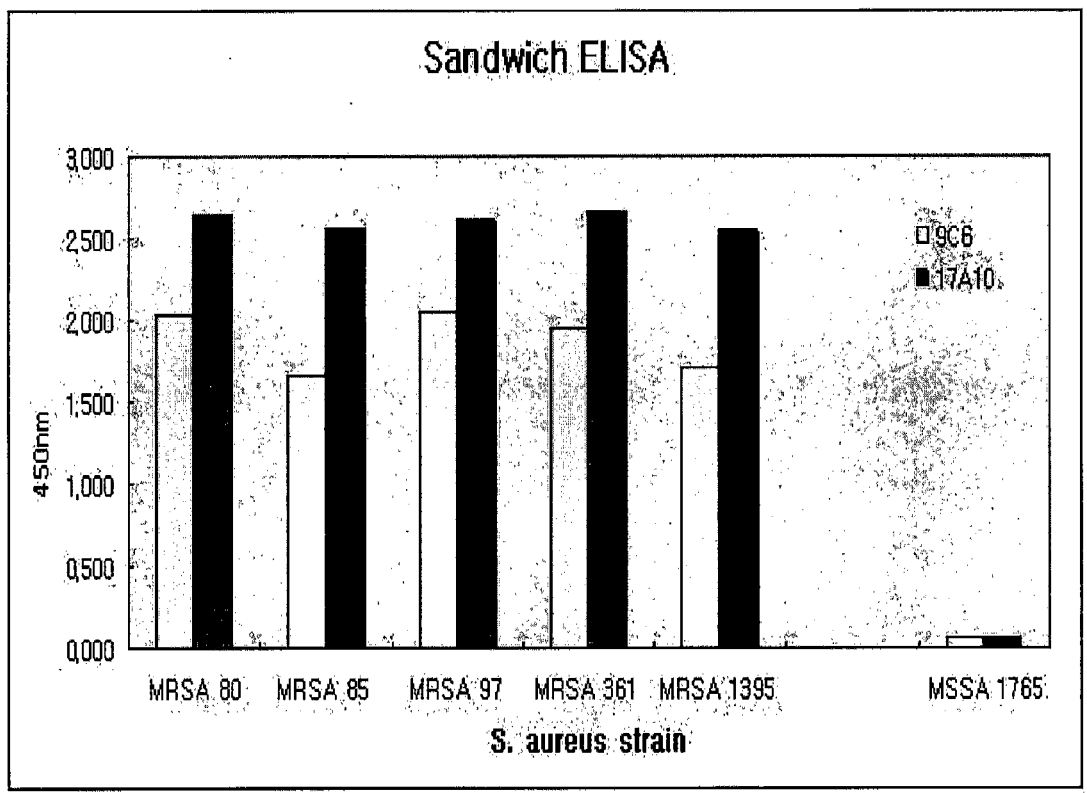
FIGS. 10a and 10b show that MRSA can be selectively detected from other Staphylococcus aureus by using the monoclonal antibodies of the present invention.

FIG. 10a indicated that the antibodies obtained from Example 2-3 effectively differentiated MRSA from MSSA, thereby effectively detected MRSA. Particularly, detection efficiency was highest where '6G10' monoclonal antibody was used as detection antibody along with '17A10' monoclonal antibody as coating antibody.

Figure 10B:
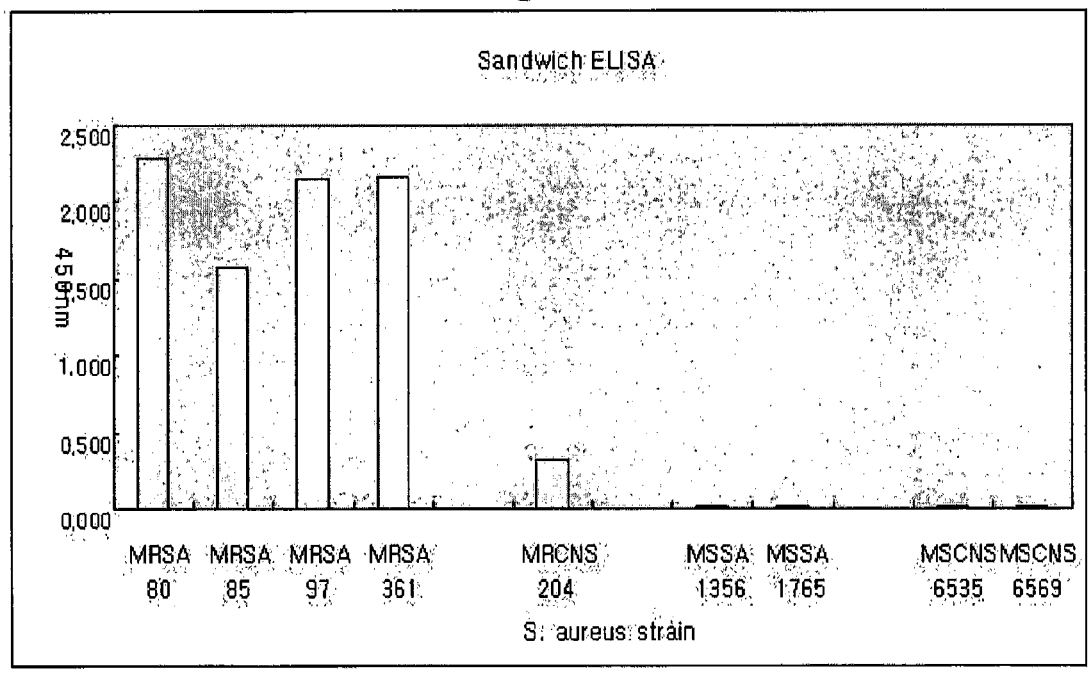

FIG. 10b showed the results in which existence of PBP2a was tested for 4 strains of MRSA, one strain of MR-CNS, and 2 strains of MSSA, and 2 strains MS-CNS, by using '6G10' monoclonal antibody as detection antibody and '17A10' monoclonal antibody as coating antibody.

FIG. 10b showed that high values were obtained for MRSA and MR-CNS, in which PBP2a exist.

<5-3> MRSA Detection with Immunochromatograph Assay Using Antibody Pairs

It was tested whether the monoclonal antibody pairs according to the embodiment of the present invention could be used for lateral flow immunographic assay in rapid kit form, which used gold conjugated detection antibody.

Detailed descriptions of the procedure are as follows. As selected among the monoclonal antibodies according to the present invention, the capture antibody was coated on the membrane, and the detection antibody was gold conjugated, dried and assembled into the device. In the assembled device, 100 ul of the lysates for each cell line as obtained from Example 4-1 was run. The result observed after 20 min was shown in FIG. 11.

Figure 11:
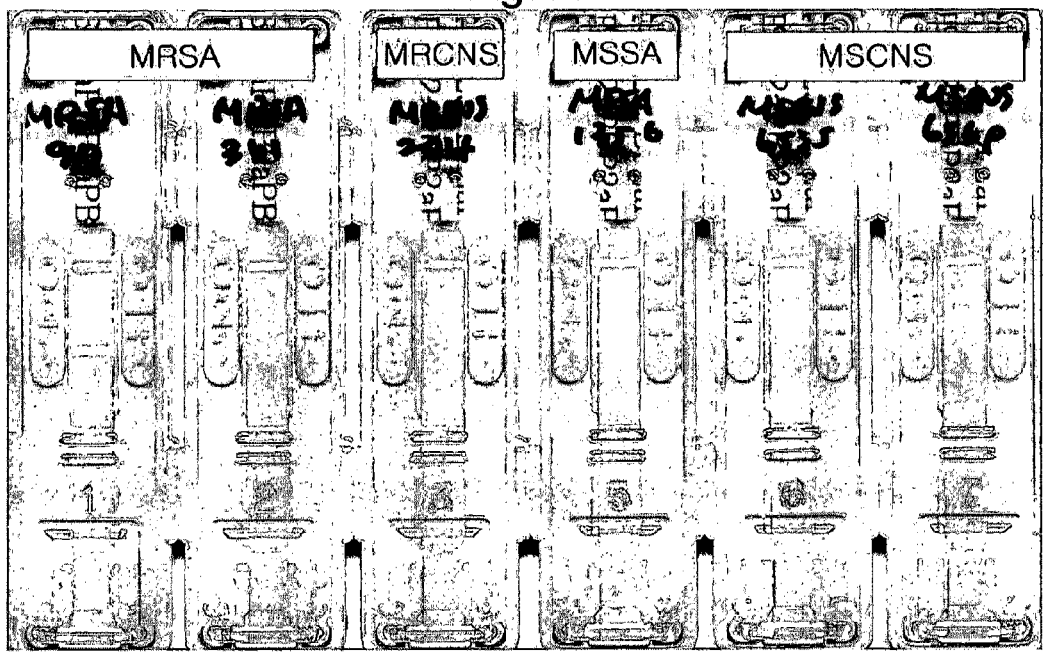
FIG. 11 shows the result for lateral flow immunoassay using an antibody pair constructed from the monoclonal antibodies of the present invention.

As indicated in FIG. 11, with the use of the monoclonal antibody pairs, positive reactions of the test lines (T) were observed at MRSA and MR-CNS, both of which have PBP2a.

EXAMPLE 6

MRSA Detection by Using Protein A-specific Polyclonal Antibody

<6-1> Selecting Protein A-Specific Polyclonal Antibody

Due to its affinity for the Fc region in many antibodies, Protein A may pose a difficulty in detection of Protein A by using antibodies. It is known, however, that anti-Protein A antibody from chicken exhibits no such binding to Protein A. Therefore, the example below was carried out using the anti-Protein A antibody from chicken (ABCPA-0500, Arista) (Larsson A, Sjöquist J. 1989; 27(12):2856-7. J Clin Microbiol./Lindmark R, Sjöquist J. 1983; 62:1-13. J. Immunol.).

<6-2> MRSA Detection with Sandwich ELISA

Maxisorp plates (Nunc.) were incubated for coating with monoclonal antibodies as capture antibody in serial dilutions with PBS (initially 100 ng/well) for one hour after each dilution at 37° C. The plates were further incubated for one hour at 37° C. in 3% BSA/PBS for blocking. The lysates from Example 4-1, serially diluted in PBS (initially 100 ng/well), were added into the wells and were incubated for one hour after each dilution at 37° C. for bindings with the coated antibodies.

After three-times of washing, rabbit anti-Protein A-HRP antibody (Sigma) was added as diluted 1:1000 with PBS into the wells (100 ul/well) and was incubated for one hour for antigen-antibody binding.

After three-times of washing again, the wells were treated with TMB solution (50 ul per well) as substrate for color reaction for 10 min. Then substrate-enzyme reaction was allowed for 10 min. The reaction was stopped with addition of stop solution (50 ul per well). The intensity of the color reaction was measured at 450 nm. The result is as shown in FIG. 12.

Figure 12:
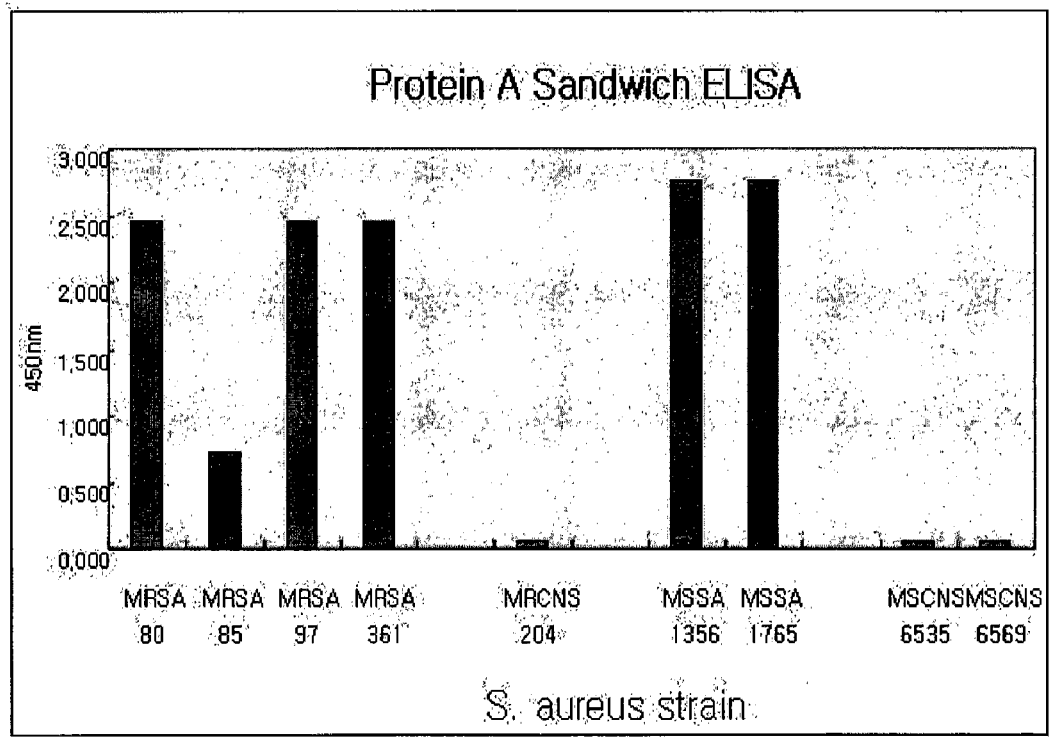
FIG. 12 shows the result by sandwich ELISA in which anti-Protein A polyclonal antibodies were used to detect presence of Protein A.

As shown in FIG. 12, high level of Protein A was observed at MRSA and MSSA, both of which strain Protein A exists.

<6-3> Immunochromatographic Assay

It was tested whether polyclonal antibody pairs against chicken Protein A as exemplified in Example 6-1 can be used for lateral flow immunographic assay in rapid kit form, which uses gold conjugated detection antibody.

Detailed descriptions of the procedure are as follows. As selected among the monoclonal antibodies according to the present invention, the capture antibody was coated on the membrane, the detection antibody was gold conjugated, dried and assembled into the device. In the assembled device, 100 ul of the lysates for each cell line as obtained from Example 4-1 was run. The result observed after 20 min is shown in FIG. 13.

Figure 13:
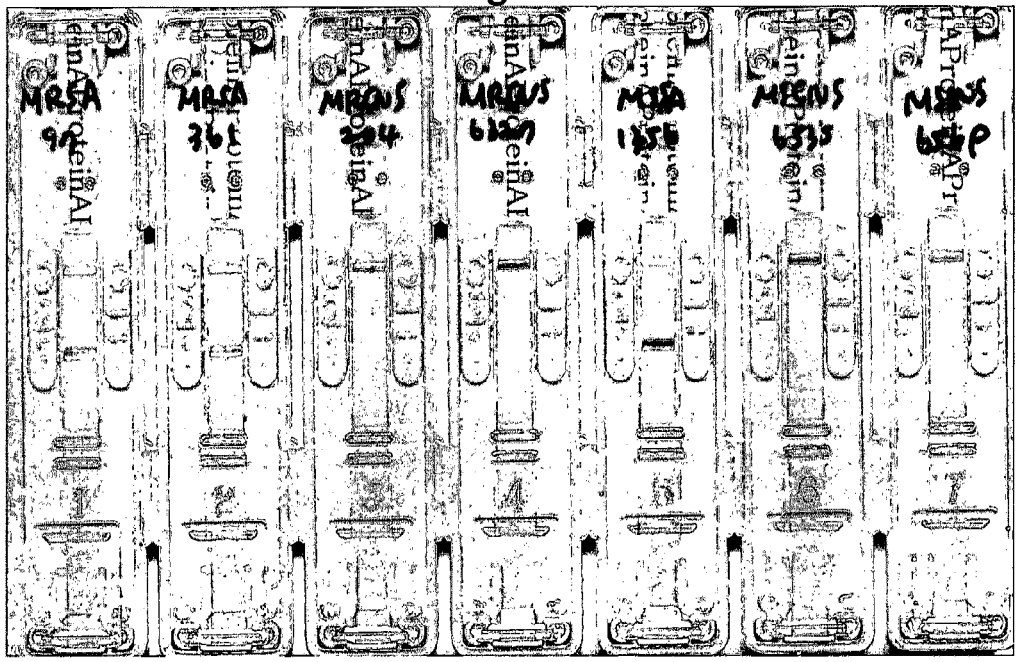
FIG. 13 shows the result lateral flow immunoassay in which anti-Protein A polyclonal antibodies were used.

As indicated in FIG. 13, positive reactions of the test lines (T) were observed only at MRSA and MSSA, both of which have Protein A.

EXAMPLE 7

MRSA Detection by Using the Monoclonal Antibodies and Protein A-specific Polyclonal Antibodies In a paired well system, anti-PBP2a monoclonal antibodies (serially diluted with PBS, initially 100 ng/well) were added into one set of the wells, while anti-Protein A polyclonal antibodies (serially diluted with PBS, initially 100 ng/well) added into the other set of wells. For coating with the antigens, Maxisorp plates (Nunc.) were incubated with the antibodies for one hour after each dilution at 37° C. The plates were further incubated for one hour at 37° C. in 3% BSA/PBS for blocking. The lysates from Example 4-1, serially diluted in PBS (initially 100 ng/well), were added into the wells and were incubated for one hour after each dilution at 37° C. for bindings with the coated antibodies.

After three-times of washing, '6G10' anti-PBP2a monoclonal-HRP antibody, diluted 1:10000 in PBS, was added into the PBP2a wells (100 ul per well). Meanwhile, rabbit anti-Protein A-HRP antibody, diluted 1:10000 in PBS, was added into the Protein A wells (100 ul per well). After three-times of washing again, the wells were treated with TMB solution (50 ul per well) as substrate for color reaction and were allowed for reaction for 10 min. The reaction was stopped with addition of stop solution (50 ul per well). The intensity of the color reaction was measured at 450 nm. The result is as shown in FIG. 14a.

Figure 14A:
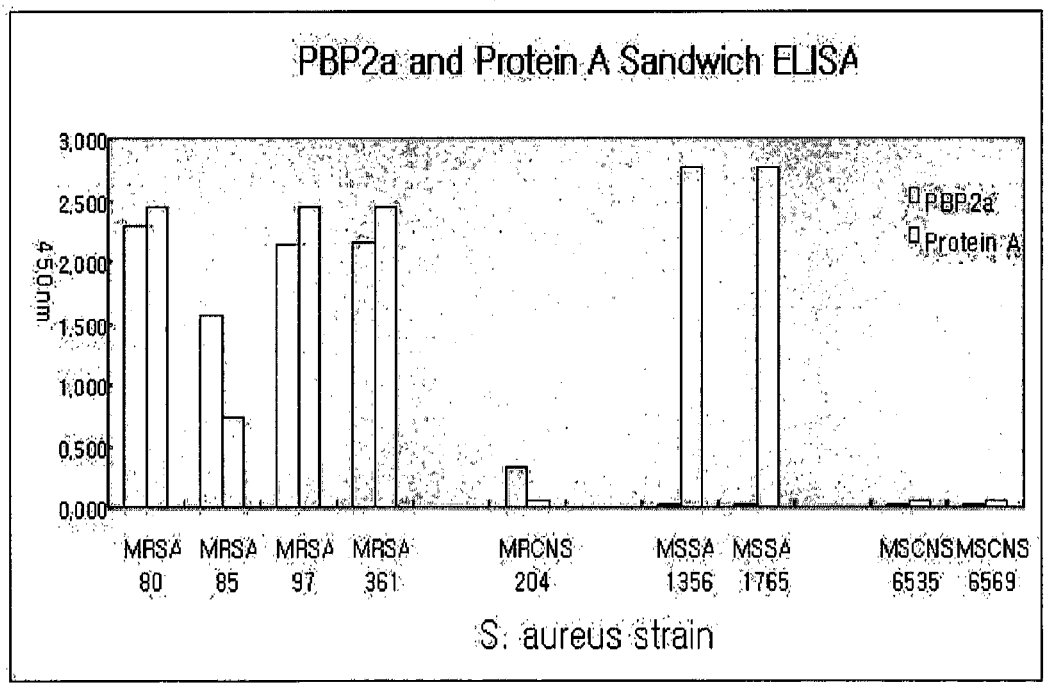
Figure 14D:
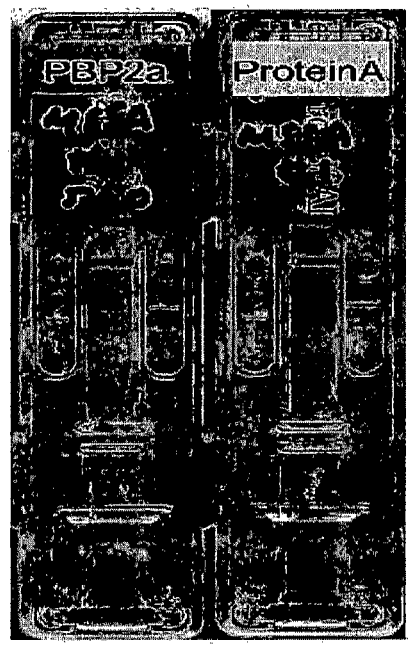
Figure 14E:
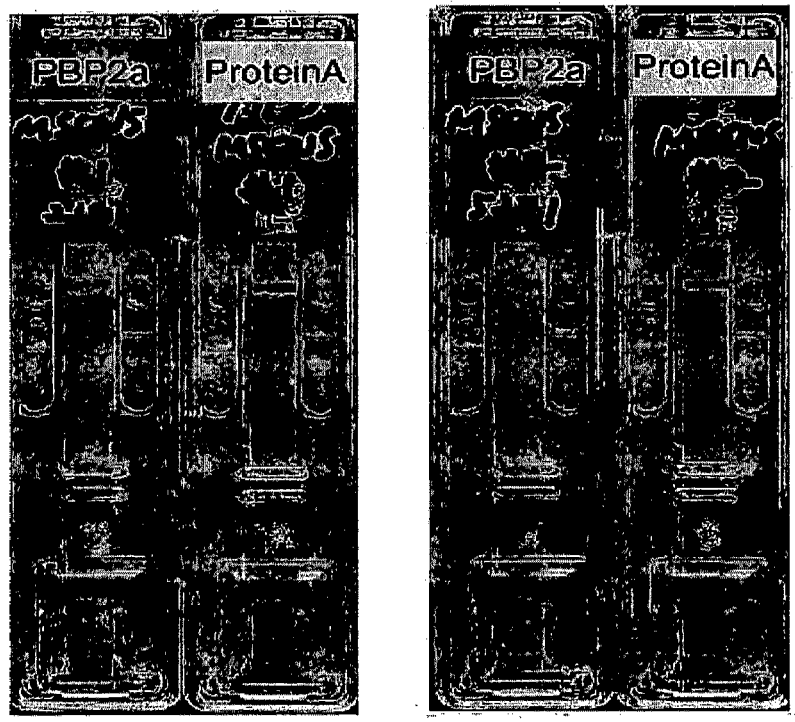

As can be seen from FIG. 14a, it was MRSA which showed high degree of reaction both to PBP2a and Protein A antigens.

In addition, a device was built for performing lateral flow immunographic assay, in which each of coating antibody and gold conjugate was assembled as suitable for PBP2a and Protein A. In the device, 100 ul of the lysates from each cell line as obtained from Example 4-1 was run. The result observed after 20 min was shown in FIGS. 14b to 14e.

As can be seen from FIGS. 14b to 14e, it was MRSA which showed high degree of reactions both to PBP2a and Protein A antigens.

The invention claimed is:

1. A method for detecting a methicillin resistant *Staphylococcus aureus*(MRSA) comprising the steps of:
    contacting a test sample with a antibody specific to the PBP2a of MRSA and a Protein A-specific antibody; and detecting the formation of an antigen-antibody complex, wherein the antibody specific to the PBP2a of MRSA is produced from a hybridoma cell deposited with the Korean Cell Line Bank under the accession number of KCLRF-BP-00202, KCLRF-BP-00203, or KCLRF-BP-00204.

2. The method according to claim 1, wherein said PBP2a-specific antibody specifically binds to a polypeptide comprising a PBP2a fragment comprising the amino acids of SEQ ID NO: 1.

3. The method according to claim 1, wherein said Protein A-specific antibody is a polyclonal antibody obtained from chicken immunized with Protein A.

4. The method according to claim 1, wherein the step of detecting the formation of an antigen-antibody complex is performed by at least a method selected from the group consisting of radioactivity immunoanalysis, enzyme-linked immunosorbent assay(ELISA), sandwich immunoanalysis, and lateral flow immunographic assay.

* * * * *

SEQUENCE LISTING

<160> NUMBER OF SEQ ID NOS: 4

<210> SEQ ID NO 1
<211> LENGTH: 330
<212> TYPE: PRT
<213> ORGANISM: Artificial Sequence
<220> FEATURE:
<223> OTHER INFORMATION: MRSA Specific-PBP2a region

<400> SEQUENCE: 1

```
Gly Ile Tyr Phe Tyr Ala Ser Lys Asp Lys Glu Ile Asn Asn Thr Ile
 1               5                   10                  15

Asp Ala Ile Glu Asp Lys Asn Phe Lys Gln Val Tyr Lys Asp Ser Ser
            20                  25                  30

Tyr Ile Ser Lys Ser Asp Asn Gly Glu Val Glu Met Thr Glu Arg Pro
        35                  40                  45
```

```
Ile Lys Ile Tyr Asn Ser Leu Gly Val Lys Asp Ile Asn Ile Gln Asp
     50                  55                  60
Arg Lys Ile Lys Lys Val Ser Lys Asn Lys Arg Val Asp Ala Gln
 65                  70                  75                  80
Tyr Lys Ile Lys Thr Asn Tyr Gly Asn Ile Asp Arg Asn Val Gln Phe
                 85                  90                  95
Asn Phe Val Lys Glu Asp Gly Met Trp Lys Leu Asp Trp Asp His Ser
                100                 105                 110
Val Ile Ile Pro Gly Met Gln Lys Asp Gln Ser Ile His Ile Glu Asn
                115                 120                 125
Leu Lys Ser Glu Arg Gly Lys Ile Leu Asp Arg Asn Asn Val Glu Leu
    130                 135                 140
Ala Asn Thr Gly Thr His Met Arg Leu Gly Ile Val Pro Lys Asn Val
145                 150                 155                 160
Ser Lys Lys Asp Tyr Lys Ala Ile Ala Lys Glu Leu Ser Ile Ser Glu
                165                 170                 175
Asp Tyr Ile Asn Asn Lys Trp Ile Lys Ile Gly Tyr Lys Met Ile Pro
                180                 185                 190
Ser Phe His Phe Lys Thr Val Lys Lys Met Asp Glu Tyr Leu Ser Asp
    195                 200                 205
Phe Ala Lys Lys Phe His Leu Thr Thr Asn Glu Thr Glu Ser Arg Asn
210                 215                 220
Tyr Pro Leu Glu Lys Ala Thr Ser His Leu Leu Gly Tyr Val Gly Pro
225                 230                 235                 240
Ile Asn Ser Glu Glu Leu Lys Gln Lys Glu Tyr Lys Gly Tyr Lys Asp
                245                 250                 255
Asp Ala Val Ile Gly Lys Lys Gly Leu Glu Lys Leu Tyr Asp Lys Lys
                260                 265                 270
Leu Gln His Glu Asp Gly Tyr Arg Val Thr Ile Val Asp Asp Asn Ser
    275                 280                 285
Asn Thr Ile Ala His Thr Leu Ile Glu Lys Lys Lys Asp Gly Lys
    290                 295                 300
Asp Ile Gln Leu Thr Ile Asp Ala Lys Val Gln Lys Ser Ile Tyr Asn
305                 310                 315                 320
Asn Met Lys Asn Asp Tyr Gly Ser Gly Thr
                325                 330
```

<210> SEQ ID NO 2
<211> LENGTH: 668
<212> TYPE: PRT
<213> ORGANISM: Artificial Sequence
<220> FEATURE:
<223> OTHER INFORMATION: PBP2a protein

<400> SEQUENCE: 2

```
Met Lys Lys Ile Lys Ile Val Pro Leu Ile Leu Ile Val Val Val Val
  1               5                  10                  15
Gly Phe Gly Ile Tyr Phe Tyr Ala Ser Lys Asp Lys Glu Ile Asn Asn
                 20                  25                  30
Thr Ile Asp Ala Ile Glu Asp Lys Asn Phe Lys Gln Val Tyr Lys Asp
             35                  40                  45
Ser Ser Tyr Ile Ser Lys Ser Asp Asn Gly Glu Val Glu Met Thr Glu
    50                  55                  60
Arg Pro Ile Lys Ile Tyr Asn Ser Leu Gly Val Lys Asp Ile Asn Ile
 65                  70                  75                  80
```

```
Gln Asp Arg Lys Ile Lys Lys Val Ser Lys Asn Lys Lys Arg Val Asp
                 85                  90                  95
Ala Gln Tyr Lys Ile Lys Thr Asn Tyr Gly Asn Ile Asp Arg Asn Val
            100                 105                 110
Gln Phe Asn Phe Val Lys Glu Asp Gly Met Trp Lys Leu Asp Trp Asp
        115                 120                 125
His Ser Val Ile Ile Pro Gly Met Gln Lys Asp Gln Ser Ile His Ile
    130                 135                 140
Glu Asn Leu Lys Ser Glu Arg Gly Lys Ile Leu Asp Arg Asn Asn Val
145                 150                 155                 160
Glu Leu Ala Asn Thr Gly Thr His Met Arg Leu Gly Ile Val Pro Lys
                165                 170                 175
Asn Val Ser Lys Lys Asp Tyr Lys Ala Ile Ala Lys Glu Leu Ser Ile
            180                 185                 190
Ser Glu Asp Tyr Ile Asn Asn Lys Trp Ile Lys Ile Gly Tyr Lys Met
        195                 200                 205
Ile Pro Ser Phe His Phe Lys Thr Val Lys Lys Met Asp Glu Tyr Leu
    210                 215                 220
Ser Asp Phe Ala Lys Lys Phe His Leu Thr Thr Asn Glu Thr Glu Ser
225                 230                 235                 240
Arg Asn Tyr Pro Leu Glu Lys Ala Thr Ser His Leu Leu Gly Tyr Val
                245                 250                 255
Gly Pro Ile Asn Ser Glu Glu Leu Lys Gln Lys Glu Tyr Lys Gly Tyr
            260                 265                 270
Lys Asp Asp Ala Val Ile Gly Lys Lys Gly Leu Glu Lys Leu Tyr Asp
        275                 280                 285
Lys Lys Leu Gln His Glu Asp Gly Tyr Arg Val Thr Ile Val Asp Asp
    290                 295                 300
Asn Ser Asn Thr Ile Ala His Thr Leu Ile Glu Lys Lys Lys Lys Asp
305                 310                 315                 320
Gly Lys Asp Ile Gln Leu Thr Ile Asp Ala Lys Val Gln Lys Ser Ile
                325                 330                 335
Tyr Asn Asn Met Lys Asn Asp Tyr Gly Ser Gly Thr Ala Ile His Pro
            340                 345                 350
Gln Thr Gly Glu Leu Leu Ala Leu Val Ser Thr Pro Ser Tyr Asp Val
        355                 360                 365
Tyr Pro Phe Met Tyr Gly Met Ser Asn Glu Glu Tyr Asn Lys Leu Thr
    370                 375                 380
Glu Asp Lys Lys Glu Pro Leu Leu Asn Lys Phe Gln Ile Thr Thr Ser
385                 390                 395                 400
Pro Gly Ser Thr Gln Lys Ile Leu Thr Ala Met Ile Gly Leu Asn Asn
                405                 410                 415
Lys Thr Leu Asp Asp Lys Thr Ser Tyr Lys Ile Asp Gly Lys Gly Trp
            420                 425                 430
Gln Lys Asp Lys Ser Trp Gly Gly Tyr Asn Val Thr Arg Tyr Glu Val
        435                 440                 445
Val Asn Gly Asn Ile Asp Leu Lys Gln Ala Ile Glu Ser Ser Asp Asn
    450                 455                 460
Ile Phe Phe Ala Arg Val Ala Leu Glu Leu Gly Ser Lys Lys Phe Glu
465                 470                 475                 480
Lys Gly Met Lys Lys Leu Gly Val Gly Glu Asp Ile Pro Ser Asp Tyr
                485                 490                 495
Pro Phe Tyr Asn Ala Gln Ile Ser Asn Lys Asn Leu Asp Asn Glu Ile
            500                 505                 510
```

```
Leu Leu Ala Asp Ser Gly Tyr Gly Gln Gly Glu Ile Leu Ile Asn Pro
        515                 520                 525

Val Gln Ile Leu Ser Ile Tyr Ser Ala Leu Glu Asn Asn Gly Asn Ile
        530                 535                 540

Asn Ala Pro His Leu Leu Lys Asp Thr Lys Asn Lys Val Trp Lys Lys
545                 550                 555                 560

Asn Ile Ile Ser Lys Glu Asn Ile Asn Leu Leu Asn Asp Gly Met Gln
                565                 570                 575

Gln Val Val Asn Lys Thr His Lys Glu Asp Ile Tyr Arg Ser Tyr Ala
            580                 585                 590

Asn Leu Ile Gly Lys Ser Gly Thr Ala Glu Leu Lys Met Lys Gln Gly
        595                 600                 605

Glu Ser Gly Arg Gln Ile Gly Trp Phe Ile Ser Tyr Asp Lys Asp Asn
        610                 615                 620

Pro Asn Met Met Met Ala Ile Asn Val Lys Asp Val Gln Asp Lys Gly
625                 630                 635                 640

Met Ala Ser Tyr Asn Ala Lys Ile Ser Gly Lys Val Tyr Asp Glu Leu
                645                 650                 655

Tyr Glu Asn Gly Asn Lys Lys Tyr Asp Ile Asp Glu
            660                 665

<210> SEQ ID NO 3
<211> LENGTH: 27
<212> TYPE: DNA
<213> ORGANISM: Artificial Sequence
<220> FEATURE:
<223> OTHER INFORMATION: MRSA Specific-PBP2a forwarding primer

<400> SEQUENCE: 3
ggaattcggt atatttttt atgcttc                                      27

<210> SEQ ID NO 4
<211> LENGTH: 25
<212> TYPE: DNA
<213> ORGANISM: Artificial Sequence
<220> FEATURE:
<223> OTHER INFORMATION: MRSA Specific-PBP2a reverse primer

<400> SEQUENCE: 4
tctcgagagt acctgagcca taatc                                       25
```